United States Patent
Moon et al.

(10) Patent No.: US 12,097,007 B2
(45) Date of Patent: Sep. 24, 2024

(54) INTERACTIVE HEALTH-MONITORING PLATFORM FOR WEARABLE WIRELESS SENSOR SYSTEMS

(71) Applicants: SAN DIEGO STATE UNIVERSITY RESEARCH FOUNDATION, San Diego, CA (US); ELECTRONICS AND TELECOMMUNICATIONS RESEARCH INSTITUTE, Daejeon (KR); Kee Moon, San Diego, CA (US); Sung Q. Lee, Seoul (KR); Woosub Youm, Seoul (KR)

(72) Inventors: Kee Moon, San Diego, CA (US); Sung Q. Lee, Seoul (KR); Woosub Youm, Seoul (KR)

(73) Assignees: San Diego State University Research Foundation, San Diego, CA (US); Electronics & Telecommunications Research Institute, Daejeon (KR)

( * ) Notice: Subject to any disclaimer, the term of this patent is extended or adjusted under 35 U.S.C. 154(b) by 435 days.

(21) Appl. No.: 17/635,696

(22) PCT Filed: Sep. 16, 2020

(86) PCT No.: PCT/US2020/051136
§ 371 (c)(1),
(2) Date: Feb. 16, 2022

(87) PCT Pub. No.: WO2021/055520
PCT Pub. Date: Mar. 25, 2021

(65) Prior Publication Data
US 2022/0287564 A1   Sep. 15, 2022

Related U.S. Application Data

(60) Provisional application No. 62/901,084, filed on Sep. 16, 2019.

(51) Int. Cl.
*A61B 5/00*   (2006.01)
*A61B 5/024*   (2006.01)
(Continued)

(52) U.S. Cl.
CPC ............ *A61B 5/0022* (2013.01); *A61B 5/024* (2013.01); *A61B 5/0816* (2013.01); *A61B 5/28* (2021.01);
(Continued)

(58) Field of Classification Search
None
See application file for complete search history.

(56) References Cited

U.S. PATENT DOCUMENTS 8,668,644 B2 * 3/2014 Ong ................. A61B 5/352
  600/509
2016/0058318 A1 * 3/2016 Borjigin ............. A61B 5/318
  600/521

(Continued)

FOREIGN PATENT DOCUMENTS

CN   106031295 B   12/2019
KR   101739542 B1   6/2017
WO   PCT/US2020/051136   9/2020

OTHER PUBLICATIONS

TLV320AIC34 Four-Channel, Low-Power Audio Codec for Portable Audio and Telephony, Oct. 2007, Texas Instruments.
(Continued)

*Primary Examiner* — Carl H Layno
*Assistant Examiner* — Manolis Pahakis
(74) *Attorney, Agent, or Firm* — JUNEAU & MITCHELL; Todd L. Juneau

(57) ABSTRACT

The embodiments described herein relate generally to medical devices that measure vital signs, and more particularly to wearable wireless devices that collect multiple simultaneous
(Continued)

vital signs, and systems and methods for compressing the sensor data into a matrix representation to facilitate collecting, transmitting, processing, and displaying vital sign data.

15 Claims, 28 Drawing Sheets

(51) Int. Cl.
  *A61B 5/08* (2006.01)
  *A61B 5/28* (2021.01)
  *A61B 5/296* (2021.01)
  *G16H 10/60* (2018.01)
  *G16H 40/67* (2018.01)
  *G16H 50/20* (2018.01)

(52) U.S. Cl.
  CPC ............ *A61B 5/296* (2021.01); *A61B 5/6813* (2013.01); *A61B 5/7232* (2013.01); *A61B 5/7235* (2013.01); *A61B 5/743* (2013.01); *A61B 5/7435* (2013.01); *G16H 10/60* (2018.01); *G16H 40/67* (2018.01); *G16H 50/20* (2018.01)

(56) References Cited

U.S. PATENT DOCUMENTS

| | | | |
|---|---|---|---|
| 2016/0278713 A1* | 9/2016 | Shoaran | A61B 5/7232 |
| 2018/0060492 A1* | 3/2018 | Feng | G16H 50/70 |
| 2020/0367773 A1* | 11/2020 | Wang | A61B 5/02405 |
| 2022/0028060 A1* | 1/2022 | Masuda | G16H 40/67 |
| 2022/0287564 A1* | 9/2022 | Moon | A61B 5/6813 |

OTHER PUBLICATIONS

ECG Measurement System, Sep. 16, 2020, Chen, Chia-Hung: Pan, Shi-Gun, Kinget, Peter.
A Wireless Wearable ECG Sensor for Long-Term Applications, Jan. 2012, IEEE Commuications Magazine.
Wearable ECG-recording System for Continuous Arrhythmia Monitoring in a Wireless Tele-Home-Care Situation, Jun. 23, 2005, IEEE International Symposium on Computer-Based Medical Systems.
Wikipedia article, "Stethoscope" Jul. 4, 2020.
Wikipedia article, "Respiratory Sounds" Aug. 31, 2020.
Wikipedia article, "Human body temperature" Sep. 15, 2020.
Wikipedia article, "Electromyography" Sep. 6, 2020.
Wikipedia article, "Electrocardiography" Sep. 12, 2020.

* cited by examiner

FLOWCHART - Phase 1

FLOWCHART - Phase 2

(a)

(b)

Signature Matrix for average =

| 70 | 8 | 22 | 30 | 80 |
|---|---|---|---|---|
| 13 | 1 | 0 | 0 | 38 |
| 26 | 0 | 0 | 0 | 68 |
| 13 | 0 | 0 | 0 | 19 |
| 24 | 5 | 10 | 5 | 58 |

Signature Matrix for std =

| 8 | 2 | 42 | 6 | 25 |
|---|---|---|---|---|
| 4 | 25 | 32 | 9 | 7 |
| 8 | 38 | 0 | 7 | 16 |
| 5 | 24 | 15 | 1 | 13 |
| 20 | 22 | 36 | 20 | 40 |

INTERACTIVE HEALTH-MONITORING PLATFORM FOR WEARABLE WIRELESS SENSOR SYSTEMS

CROSS-REFERENCE TO RELATED APPLICATIONS

This application is a National Stage Application of PCT/US20/51136 filed Sep. 16, 2020, which claims priority benefit to U.S. Provisional Patent Application No. 62/901,084 filed Sep. 16, 2019 entitled Hierarchical health-monitoring platform for wearable wireless sensor systems", the disclosure of which is incorporated herein by reference in its entirety.

BACKGROUND

The embodiments described herein relate generally to medical devices that measure vital signs, and more particularly to wearable wireless devices that collect multiple simultaneous vital signs, and systems and methods for compressing the sensor data into a matrix representation to facilitate collecting, transmitting, processing, and displaying vital sign data.

Accurate measurement and monitoring of physiological parameters play an essential role in a broad range of applications in healthcare, psycho-physiological examinations, and sports training. In the past, there have been health monitoring devices that are either complex health monitoring devices performed in a laboratory environment with wired laboratory facilities or simple wearable health monitoring devices that are single channel wireless devices to record heartbeat or body motion. Accordingly a need exists for a comprehensive wearable sensor system to monitor multiple physiological signals simultaneously to monitor various health conditions.

SUMMARY

The embodiments described herein are directed to medical devices that measure vital signs, and more particularly to wearable wireless devices that collect multiple simultaneous vital signs, and systems and methods for collecting, transmitting, processing, and displaying vital sign data.

The present disclosure relates to a remote continuous monitoring device, a sensor signal processing algorithm, which can improve the performance of the following hierarchical decision steps: improved sensor data observation (normal vs. abnormal) using a specially configured on-body microprocessor, improved evaluation of abnormal sensor data (healthy vs. no healthy) on a local computer, improved decision-making about medical intervention (intervention vs. nonintervention) on a healthcare provider server.

This invention describes a multi-sensor multi-channel wearable platform for smart remote health monitoring to address the following limitations: Diagnosis capability using a multi-sensor and multi-channel wearable system; Burdens on the local data storage at the user's site as well as at healthcare providers; and High power consumption due to the continuous flow of the massive sensor data through wireless data transmission.

The health monitoring system is the state-of-the-art technology developed to meet one of the fastest-growing medical research and markets due to the increasing aging population and associated diseases. The new small wearable wireless platform will connect patients and healthcare providers continuously and remotely with the most advanced diagnostic and data transmission technology.

DETAILED DESCRIPTION

Figure 1:
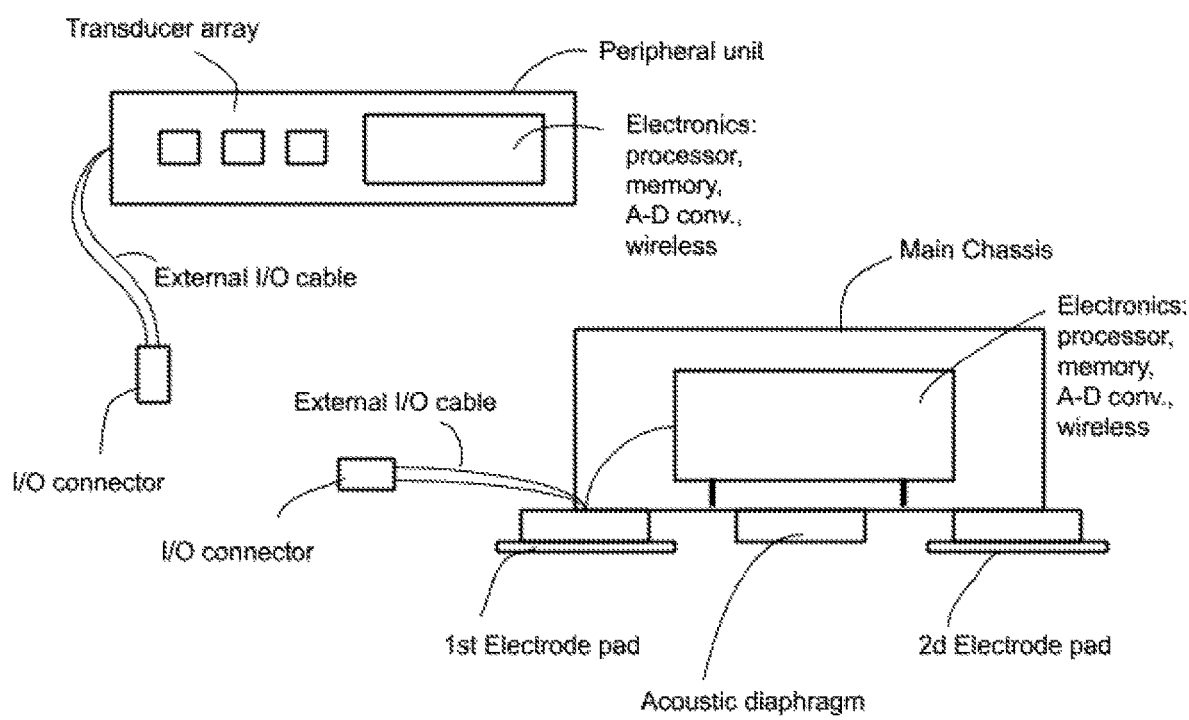
FIG. 1 is a front view schematic illustration of a multi-sensor multi-channel wearable platform for smart remote health monitoring (also referred to herein as "wearable wireless medical multisensor"), according to an embodiment.

Disclosed embodiments are directed to a new sensor system having a compression feature that can monitor heart valves sound, lung movements, electrocardiogram (ECG), and electromyogram (EMG) of breathing muscles simultaneously.

In some embodiments, the invention provides two new sensor prototypes that can monitor heart valves sound, lung movements, electrocardiogram (ECG), and electromyogram (EMG) of breathing muscles simultaneously.

In some embodiments, the invention provides an interactive health-monitoring platform for wearable wireless sensor systems.

In some embodiments, the invention provides a two-dimensional "image-like" signature matrix patterns from the sensors in order to compress the amount of sensor data and provide real-time continuous streaming, allow machine learning to facilitate alerting of patient conditions because of the use of matrix representation, and provide diagnostic options and patient instructions based on matrix representation for easy viewing and immediate comprehension.

In some embodiments, the invention provides novel signature matrix patterns that reflect the sensor's compressed characteristics per sampling window.

In some embodiments, the invention provides signature matrix patterns generated over time from a series of the frames, and providing deeper insight from the formation of frames into (Frame) Groups.

Technical Problem

The drive toward increased the remote monitoring performance by adding multi-sensor and multi-channel can place additional burdens on the local data storage at the user's site and healthcare providers. The massive sensor data's continuous flow will require a high-performance wireless data transmission technology high power consumption. Further, the constant flow of extensive patient data can expect a dedicated team of health care providers to handle the information. It can instead increase the workload of healthcare providers.

Disclosed embodiments are directed to a computer implemented system for continuous monitoring of patient health data, comprising: (i) a main on-body component attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter, (ii) a peripheral on-body component attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module, (iii) a local wireless access component having an internet connection, (iv) a health data server computer having a database and having program instructions saved to memory and executable by a processor for receiving, manipulating, storing, and transmitting patient health data, (v) Computer program instructions saved to memory and executable by the main on-body component microprocessor for performing the following steps in order:

STEP 1—Provision connection to the peripheral on-body component and provisional connection between the main on-body component and the health data server computer, STEP 2—Obtain initial sensor data, including heart sound, ECG, lung sound, EMG, EEG, EOG, temp, orientation x-y-z axis data, STEP 3—Performing any signal processing (amplification, filtering, converting) of sensor data, Collecting initial sensor data in subgroups of <100 data points at a continuous sampling window frequency (t1+n), e.g. 4 KHz, STEP 4—Calculating mean and standard deviation values from subgroups at period (t1), Converting each (t1) subgroup value to a (t1) matrix pixel value, STEP 5—Generating an N×N (t1) matrix of (t1) matrix pixel values to generate a (t1) signature sensor signal pattern (standard), STEP 6—Continuously calculating subgroup values at periods (t1+n), Converting subgroup values to matrix pixel values, Generating N×N matrix of (t1+n) m.p. values, Generating (t1+n) sensor signal pattern(s), STEP 7—Comparing (t1+n) sensor signal pattern(s) vs. (t1) signature sensor signal pattern, and STEP 8—Wirelessly transmitting to the health data server the comparison of (t1+n) sensor signal pattern(s) vs. (t1) signature sensor signal pattern.

In some disclosed embodiments, the invention is directed to a computer implemented system, wherein the computer program instructions readable by the main on-body component microprocessor stored to memory are configured to perform the following additional steps in order:

STEP 9—Receiving at a health data server a comparison of (t1+n) sensor signal matrix pattern(s) vs. (t1) signature sensor signal matrix pattern from a wireless multi-sensor continuous vital sign monitoring device, STEP 10—PerformING a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection, and STEP 11—Outputting to a patient communication device or healthcare provider access computer the best fit matching results, and providing intervention instructions related to the diseases or disorders selected from pulmonary, cardiac, neurological, cardiovascular, orthopedic, pain, immune, and infection from the stored diagnostic array of sensor signal matrix patterns.

In some disclosed embodiments, the invention is directed to a computer implemented system, the computer program instructions saved to memory and executable by the main on-body component microprocessor configured to perform the following additional steps in order:

STEP 9—Receiving at a health data server a comparison of (t1+n) sensor signal matrix pattern(s) vs. (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and std. dev. values from subgroups at period (t1) that form the (t1) matrix pixel value, and values from subgroups at periods (t1+n) that form the (t1+n) matrix pixel value, STEP 10—Identifying in a clickable display and click on one or more of the pixel(s) from the (t1+n) matrix pixel value of the (t1+n) sensor signal matrix pattern having a large period-by-period change to obtain the raw mean and std dev values from sensor data subgroups to identify the specific sensors and times providing the large period-by-period change values, and STEP 11—Outputting to a patient communication device or healthcare provider access computer change-specific patient intervention instructions related to the specific sensors and times of the large period-by-period changes.

In some implementations, the computer implemented system includes wherein the peripheral on-body-component is attached to a patient at a location selected from: hip, knee, neck, arm, wrist, forehead, occipital region, sternum, and shoulder.

In some implementations, the computer implemented system includes two or more peripheral on-body-components, wherein the two or more peripheral on-body-components are attached to a patient at different locations selected from: hip, knee, neck, arm, wrist, forehead, occipital region, sternum, and shoulder.

Non-Transitory Computer Readable Medium

Further disclosed embodiments are directed to a non-transitory computer readable medium having program instructions embodied therewith for continuous monitoring of patient health data, said program instructions comprising the steps:

Provisioning connection between a main on-body component and a peripheral on-body component and provisioning connection between the main on-body component and a health data server computer, wherein the main on-body component attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter, wherein the peripheral on-body component attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module, Connecting the main on-body component to a local wireless access component having an internet connection, and connecting the main on-body component to a health data server computer having a database and having program instructions saved to memory and executable by a processor for receiving, manipulating, storing, and transmitting patient health data, Obtaining initial sensor data from the main and peripheral on-body components, the initial sensor data comprising heart sound, ECG, lung sound, EMG, EEG, EOG, temp, and orientation x-y-z axis, Collecting initial sensor data in subgroups of <100 data points at a continuous sampling window frequency (t1+n), said frequency selected from 4 KHz, 1-10 KHz, 2 KHz, and 1-20 KHz, Calculating mean and standard deviation values from subgroups at period (t1), and Converting each (t1) subgroup value to a (t1) matrix pixel value, Generating an N×N (t1) matrix of (t1) matrix pixel values to generate a (t1) signature sensor signal pattern (standard), Continuously calculating subgroup values at periods (t1+n), and Converting subgroup values to matrix pixel values, Generating an N×N matrix of (t1+n) matrix pixel values, and Generating a (t1+n) sensor signal pattern(s) from said (t1+n) matrix pixel values, Comparing (t1+n) sensor signal pattern(s) against the (t1) signature sensor signal pattern, and Wirelessly transmitting to the health data server the comparison of (t1+n) sensor signal pattern(s) against the (t1) signature sensor signal pattern.

In some disclosed embodiments, the invention is directed to non-transitory computer readable medium, wherein the computer program instructions perform the following additional steps in order:

Receiving at a health data server a comparison of (t1+n) sensor signal matrix pattern(s) against the (t1) signature sensor signal matrix pattern from a wireless multi-sensor continuous vital sign monitoring device, Performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection, and Outputting to a patient communication device or healthcare provider access computer the best fit matching results, and provide intervention instructions related to the diseases or disorders selected from pulmonary, cardiac, neurological, cardiovascular, orthopedic, pain, immune, and infection from the stored diagnostic array of sensor signal matrix patterns In some disclosed embodiments, the invention is directed to non-transitory computer readable medium, wherein the computer program instructions perform the following additional steps in order:

Receiving at a health data server a comparison of (t1+n) sensor signal matrix pattern(s) against the (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and std. dev. values from subgroups at period (t1) that form the (t1) matrix pixel value, and values from subgroups at periods (t1+n) that form the (t1+n) matrix pixel value, Identifying in a clickable display and clicking on one or more of the pixel(s) from the (t1+n) matrix pixel value of the (t1+n) sensor signal matrix pattern having a large period-by-period change to obtain the raw mean and standard deviation values from sensor data subgroups to identify the specific sensors and times providing the large period-by-period change values, and Outputting to a patient communication device or healthcare provider access computer change-specific patient intervention instructions related to the specific sensors and times of the large period-by-period changes.

In some embodiments, the non-transitory computer readable medium includes wherein the peripheral on-body-component is attached to a patient at a location selected from: hip, knee, neck, arm, wrist, forehead, occipital region, sternum, and shoulder.

In some embodiments, the non-transitory computer readable medium includes two or more peripheral on-body-components, wherein the two or more peripheral on-body-components are attached to a patient at different locations selected from: hip, knee, neck, arm, wrist, forehead, occipital region, sternum, and shoulder.

Computer implemented methods.

In one preferred embodiment, the invention provides a computer implemented method for continuous monitoring of patient health data, comprising:

Providing a main on-body component attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter, Providing a peripheral on-body component attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module, Providing a local wireless access component having an internet connection, Providing a health data server computer having a database and having program instructions saved to memory and executable by a processor for receiving, manipulating, storing, and transmitting patient health data, Providing computer program instructions saved to memory and executable by the main on-body component microprocessor for performing the following steps in order:

Provisioning connection between a main on-body component and a peripheral on-body component and provisioning connection between the main on-body component and a health data server computer, Obtaining initial sensor data from the main and peripheral on-body components, the initial sensor data comprising heart sound, ECG, lung sound, EMG, EEG, EOG, temp, and orientation x-y-z axis, Collecting initial sensor data in subgroups of <100 data points at a continuous sampling window frequency (t1+n), said frequency selected from 4 KHz, 1-10 KHz, 2 KHz, and 1-20 KHz, Calculating mean and standard deviation values from subgroups at period (t1), and Converting each (t1) subgroup value to a (t1) matrix pixel value, Generating an N×N (t1) matrix of (t1) matrix pixel values to generate a (t1) signature sensor signal pattern (standard), Continuously calculating subgroup values at periods (t1+n), and Converting subgroup values to matrix pixel values, Generating an N×N matrix of (t1+n) matrix pixel values, and Generating a (t1+n) sensor signal pattern(s) from said (t1+n) matrix pixel values, Comparing (t1+n) sensor signal pattern(s) against the (t1) signature sensor signal pattern, and Wirelessly transmitting to the health data server the comparison of (t1+n) sensor signal pattern(s) against the (t1) signature sensor signal pattern.

In some embodiments, the computer implemented method includes the computer program instructions readable by the main on-body component microprocessor stored to memory are configured to perform the following additional steps in order:

Receiving at a health data server a comparison of (t1+n) sensor signal matrix pattern(s) against the (t1) signature sensor signal matrix pattern from a wireless multi-sensor continuous vital sign monitoring device, Performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection, and Outputting to a patient communication device or healthcare provider access computer the best fit matching results, and provide intervention instructions related to the diseases or disorders selected from pulmonary, cardiac, neurological, cardiovascular, orthopedic, pain, immune, and infection from the stored diagnostic array of sensor signal matrix patterns.

In some embodiments, the computer implemented method includes wherein the computer program instructions readable by the main on-body component microprocessor stored to memory are configured to perform the following additional steps in order:

Receiving at a health data server a comparison of (t1+n) sensor signal matrix pattern(s) against the (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and std. dev. values from subgroups at period (t1) that form the (t1) matrix pixel value, and values from subgroups at periods (t1+n) that form the (t1+n) matrix pixel value, Identifying in a clickable display and clicking on one or more of the pixel(s) from the (t1+n) matrix pixel value of the (t1+n) sensor signal matrix pattern having a large period-by-period change to obtain the raw mean and standard deviation values from sensor data subgroups to identify the specific sensors and times providing the large period-by-period change values, and Outputting to a patient communication device or healthcare provider access computer change-specific patient intervention instructions related to the specific sensors and times of the large period-by-period changes.

In some embodiments, the computer implemented method includes wherein the peripheral on-body-component is attached to a patient at a location selected from: hip, knee, neck, arm, wrist, forehead, occipital region, sternum, and shoulder.

In some embodiments, the computer implemented method includes two or more peripheral on-body-components, wherein the two or more peripheral on-body-components are attached to a patient at different locations selected from: hip, knee, neck, arm, wrist, forehead, occipital region, sternum, and shoulder.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise.

Disclosed herein is a solution to existing problem of providing a wearable multi-sensor, multi-channel vital sign sensing device having a data compression feature. The solution generally involves hardware, namely a multi-sensor multi-channel wireless sensor, Phase 1 sensor data compression and observation and Phase 2 Evaluation of abnormal health data.

Remote patient monitoring is to enable continuous monitoring of patients outside of hospital or lab settings. The performance of a remote patient monitoring technology is heavily dependent on the environment in which it operates and the accuracy of the health data that is required to produce. Therefore, it is desired to synthesize the multiple sensor data can provide more accurate and precise estimates of the health status. The invention can observe the following health data from a wearable sensor system: (1) muscle activity (EMG), (2) acoustic activity (contact microphone), (3) brain activity (EEG), (4) eye activity (EOG), and (5) skin temperature. For example, the invention employs new wearable sensor technology that uses a novel integration of acoustics and biopotentials to monitor a variety of vital signs. The new sensor can monitor heart valves sound, lung movements, electrocardiogram (ECG), and electromyogram (EMG) of breathing muscles simultaneously. (See FIGS.

Provided herein is a new sensor that can monitor heart valves sound, lung movements, electrocardiogram (ECG), and electromyogram (EMG) of breathing muscles simultaneously.

In some implementations, two new sensor prototypes are provided that can monitor heart valves sound, lung movements, electrocardiogram (ECG), and electromyogram (EMG) of breathing muscles simultaneously.

In some implementations, an interactive health-monitoring platform for wearable wireless sensor systems is provided.

Phase 1: sensor data observation

Phase 1 conducts the following computations to recognize the data packet to send it to a local computer for the next level of hierarchical decision (i.e., healthy vs. no healthy). This invention aims to provide an apparatus and method for comprehensive health status monitoring with sensor triggered patient interaction (See FIGS. 1-8).

This invention also describes in FIGS. 9-25 an algorithm for the automatic recognition of normal and abnormal status from multiple health-monitoring sensors. For example, it is well-known for many years that the respiration cycles and heartbeats are tightly coupled. Thus, the monitoring and analysis of respiration data and heart rate remotely and continuously provide essential healthcare information for the users and the public healthcare communities, including hospitals. In particular, assessment of cyclical fluctuations of heart rate, combined with the study of respiration-disorders, allows reliable recognition of the signs of illness such as coronavirus disease, etc.

However, one of the main challenges in managing multiple sensors (or channels) is the continuously generated a large amount of data. The storage of the data is not only costly but also results in subsequent work to identify the abnormal signal pattern from the vast amount of the normal (i.e., healthy) signals. The invention reduces the cost of storing the sensor data and improves the accuracy of identifying the abnormal signs from the sensors' set.

In this invention, the method is the technology developed to meet a real-time monitoring process that carries some challenges such as synthesizing the data from multiple sensors (or channels) to estimate the comprehensive state of the data. It can expand the method for multi-channel or multi-sensor signal fusion. The core of the technique is the two-dimensional "image-like" signature matrix pattern from the sensor signals. These signature matrix patterns reflect the person's compressed characteristics per given data length of interest. A real-time sensor data assessment can be conducted by comparing the person's measured signature matrix patterns (i.e., targets) with the stored patterns (i.e., templates).

The system can generate a series of two-dimensional "image-like" signature matrix patterns from the sensors. These signature matrix patterns reflect the patient's compressed characteristics per sampling window using the calculate probabilities as pixels of an image frame (See FIGS. 4, 5). A real-time sensor data assessment can be conducted by comparing the person's measured signature matrix patterns with the stored patterns.

Figure 9:
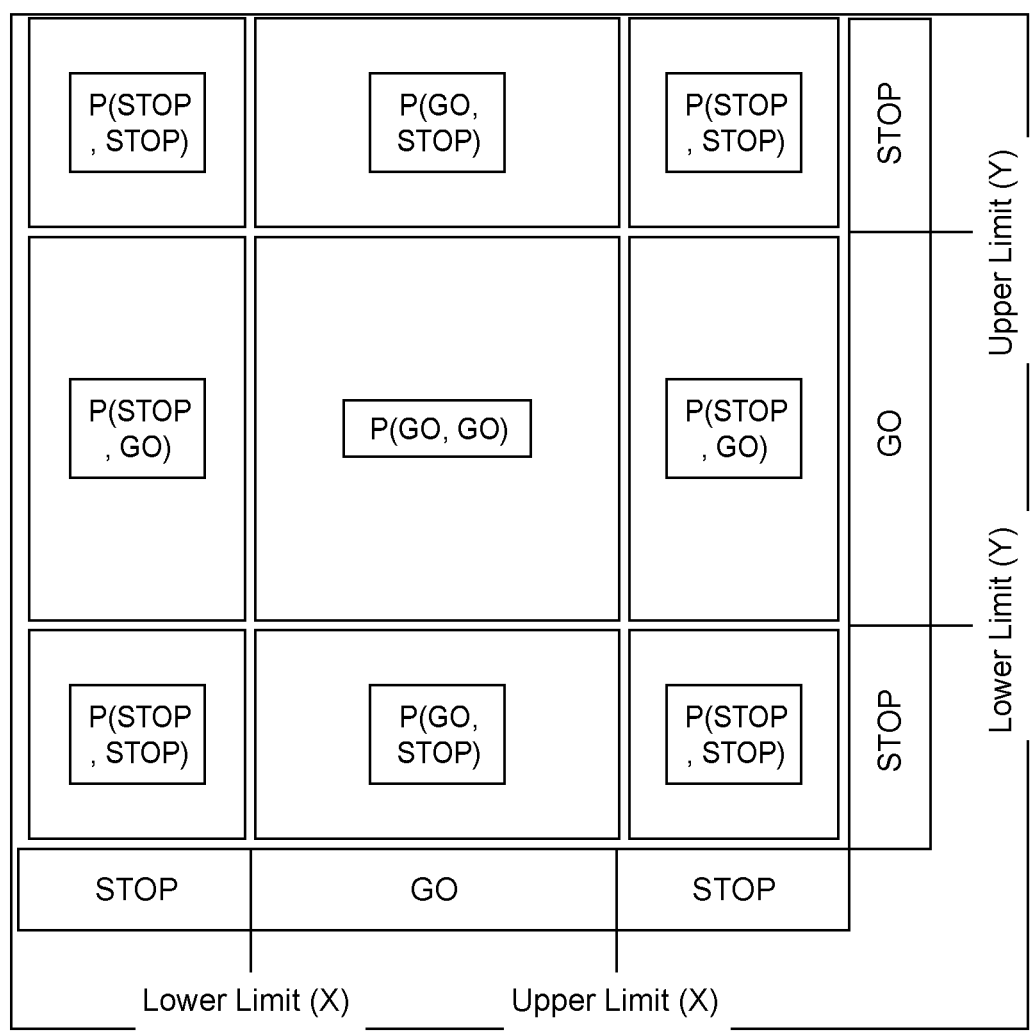
FIG. 9 is a graphical representation of a two-dimensional sensor signal pattern, signature or ongoing, created from the subgroup data points, according to an embodiment.

Referring now to FIG. 9, the two-dimensional "image-like" signature matrix patterns from the sensors.

Classification zone set-up:

A set of well-planned series of subgroups (i.e., template) is used to estimate the characteristic (or signature) behavior of the means and standard deviations of a sensor signal pattern. The method identifies the ordinary samples generated from non-intentional white noise or systematic noise of the sensor system by producing the classification zone for the means and standard deviations of each group. When a point is within the classification zone of "GO," it designates the ordinary (or noise) sample. The classification zone can be set up using the statistical control chart formula if necessary.

Calculation of Pixels of a Frame:

The signature matrix can be described as a two-dimensional probability diagram (or image map) with a N×N matrix (e.g., a 3×3 matrix is the smallest size), with a count at column j and row i. The method uses a subgroup (e.g., raw or filtered sensor signals) as a data point. Typically, the data are collected in a subgroup size of less than 100 data points. For example, there will be 40 subgroups per second if the sensor's sampling frequency is 4K Hz, which is the sampling frequency used for the sensor signal monitoring. The method calculates signature matrix pixel values from the average and standard deviation values. It looks for changes in the average and standard deviation values of sensor signals as time goes on. The method starts with dividing the signal averages and standard deviations into zones. A combination of the signal average and standard deviation from a subgroup of the data finds the corresponding pixel in the signature matrix (See FIGS. 4, 5), calculate a new pixel value, and assign the new probability value to the matrix pixel.

Figure 10:
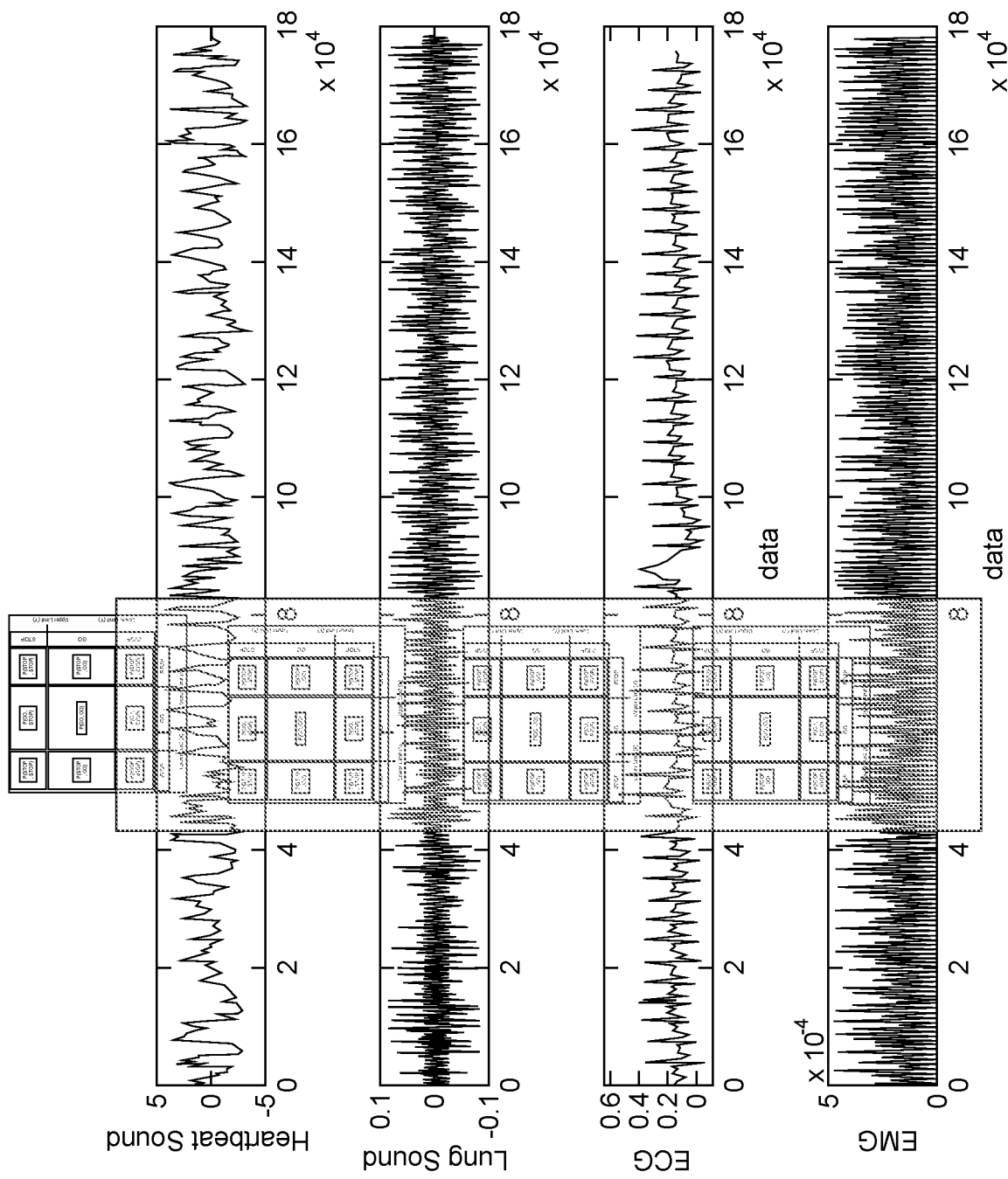
FIG. 10 is a graphical representation of signal matrix patterns reflecting the visualization of data compression per sampling period or frame, according to an embodiment.

Referring now to FIG. 10, there is provided signature matrix patterns that reflect the sensor's compressed characteristics per sampling window.

For all sensor channels, a signature matrix (i.e., frame) $SIG_k$ for data packet k with the

MATRIX $$SIG_k^{\square} = \begin{bmatrix} sig_{11}^{\square} & sig_{12}^{\square} & . & . & sig_{1N}^{\square} \\ sig_{21}^{\square} & sig_{22}^{\square} & . & . & sig_{2N}^{\square} \\ . & . & sig_{ij}^{\square} & . & . \\ . & . & . & . & . \\ sig_{N1}^{\square} & sig_{N2}^{\square} & . & . & sig_{NN}^{\square} \end{bmatrix}$$

$sig_{ij}^{\square} = P[\text{a sample mean } \bar{x} \text{ belongs to class } j) \cap$ $\square(\text{a sample standard deviation } s \text{ belongs to class } i)$ For a selected combination of the sample mean and the standard deviation (i.e., say channels X and Y), a frequency count can be calculated from a matching column j and row i whenever there is a channel X zone the corresponding zone of channel Y. Thus, a signature matrix is a probability map that a subgroup (or sample) can fall into a specific class of the subgroup means and standard deviations. The series of the frames (signature matrices) forms a group (See FIG. 6). For example, a group of signature matrices (frames) from "normal" sensor signals can be trained as a "template" using a proper training algorithm such as an artificial neural network, etc.

Figure 11:
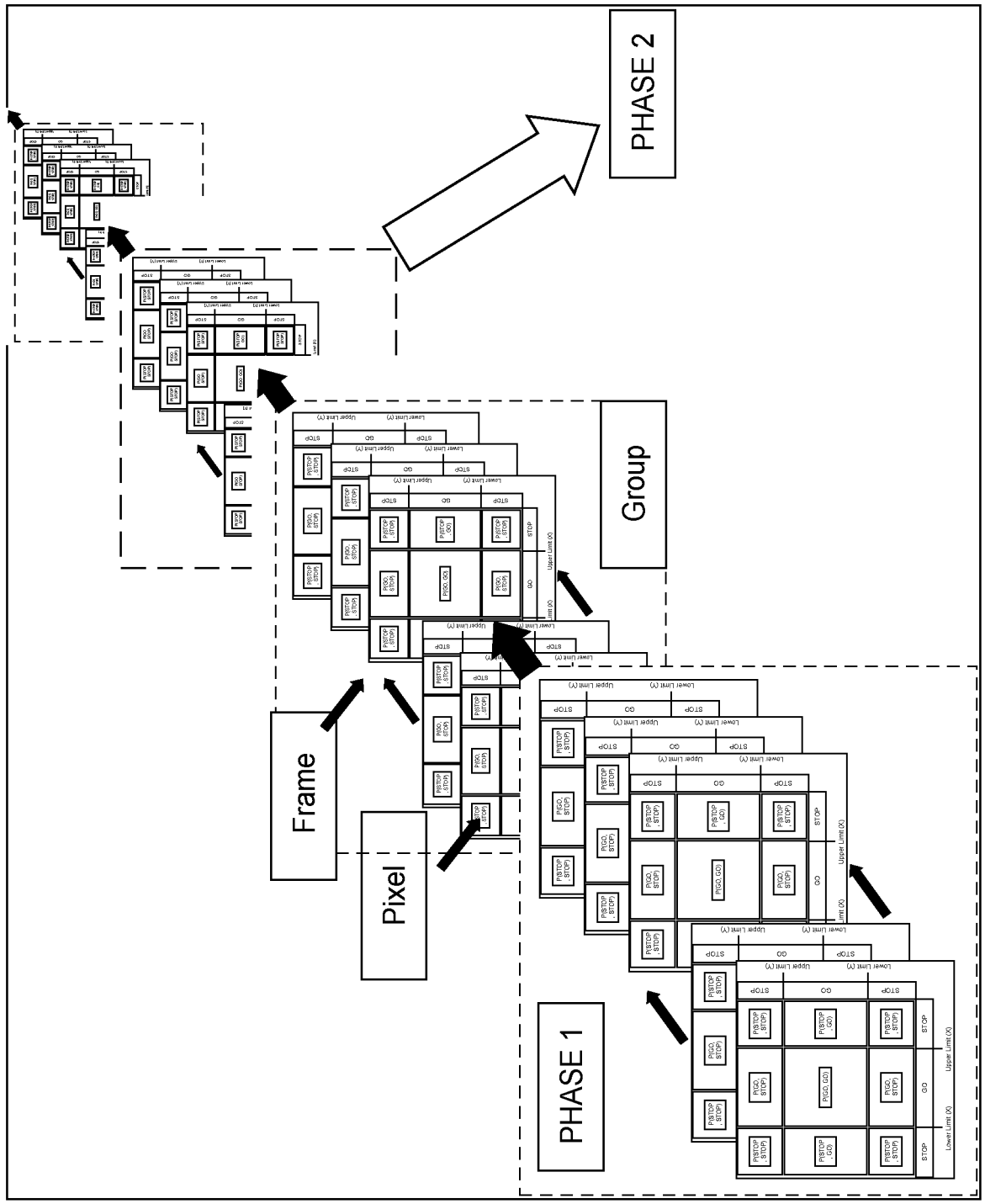
FIG. 11 is a graphical representation of a Group that is formed from a series of signature matrix patterns, according to an embodiment.

Referring now to FIG. 11, there is provided signature matrix patterns that the series of the frames forms a group. Continuous Monitoring:

If setting up a template is done, the method continues running and check the next group of frames using a proper testing algorithm, such as an artificial neural network. If the group is outside the normal range (e.g., the difference between the sample group and the template), the associated signature matrices and the signal data packet will be wirelessly transmitted to an external computer for PHASE 2 (See FIG. 11).

Phase 2: Evaluation of abnormal health data

The advanced analysis of the abnormal health data can be done in Phase 2 for diagnosis and action (including a user interaction). For example, the respiratory and cardiovascular physiological effects can help model the breathing pattern such as respiratory rate, tidal volume, and diaphragmatic activation more precisely. In this phase, the external computer can synthesize and analyzes the wirelessly transmitted healthcare data. Further, Phase 2 delivers medical decision-making such as intervention vs. no intervention decision through the diagnosis (i.e., machine learning such as ANN with patients' health history data). In this phase, the signature matrices obtained from the sensors will be utilized for the diagnosis. The diagnosis will be notified to the user for the patient's input (See FIG. 8).

Any of the wearable wireless medical monitors and/or components thereof may be fabricated from any suitable biocompatible material or combination of materials. For example, an outer chassis, and/or components thereof may be fabricated from biocompatible materials, metals, metal alloys, polymer coated metals, and/or the like. Suitable biocompatible materials, metals and/or metal alloys can include polymers, co-polymers, ceramics, glasses, aluminum, aluminum alloys, stainless steel (e.g., 316 L stainless steel), cobalt chromium (Co—Cr) alloys, nickel-titanium alloys (e.g., Nitinol®), and/or the like. Moreover, any of the chassis or components may be covered with a suitable polymer coating, and can include natural or synthetic rubber, polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

The terminology used herein is for the purpose of describing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

The examples and/or embodiments described herein are intended merely to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise.

Any of the embodiments disclosed herein may be used to treat or diagnose diseases or disorders selected from pulmonary, cardiac, neurological, cardiovascular, orthopedic, pain, immune, and infection. Pulmonary diseases include without limitation lung disease, COPD, asthma and bronchitis. Cardiac diseases and disorders include without limitation tachycardia, bradycardia, cardiomyopathy, atherosclerosis, and disorders and disease relating to arterial or venous insufficiency and problems associated with valve function. Neurological disorders include without limitation Alzheimers, Parkinsons, balance related disorders, restless leg syndrome, seizures, brain injury, anxiety, headache, and multiple sclerosis. Orthopedic diseases and disorders include without limitation rehabilitation from injury or surgery, spinal disorders, arthritis, gait-related diseases and disorders Immune related or infectious related diseases or disorders are also considered within the scope of the invention.

FIGURES

FIG. 1 is a front view schematic illustration of a multi-sensor multi-channel wearable platform for smart remote health monitoring 100 (also referred to herein as "wearable wireless medical multisensor"), according to an embodiment. FIG. 1 shows main chassis 110 having an electronics module 112 for providing an on-body processor, memory, signal processing, and wireless communication. FIG. 1 shows the main chassis 110 having a first and second electrode pad 114, 116, an acoustic diaphragm type sensor 118, and an external I/O cable 111 to connect to one or more peripheral units 120. FIG. 1 also shows peripheral unit 120 having electronics 122, with optional processing, and wireless communication. Peripheral unit 120 has a transducer array 124 or an array of multiple sensors or electrodes. Peripheral units 120 may connect to the main component 110 by wire or wirelessly.

Figure 2A:
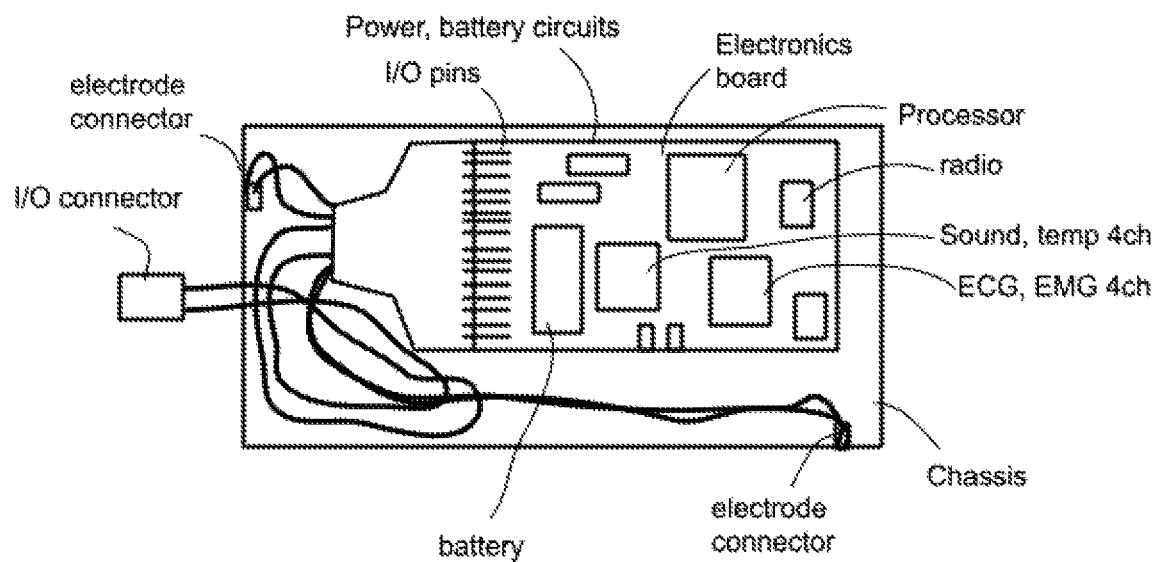
FIG. 2A is a schematic illustration of a top view of a main on-body component of a multi-sensor multi-channel wearable platform for smart remote health monitoring, according to an embodiment.

FIG. 2A is a schematic illustration of a top view of a main on-body component of a multi-sensor multi-channel wearable platform for smart remote health monitoring, according to an embodiment. FIG. 2A shows the main on-body component (OBC) having an electronics circuit board 112 with a processor 130, a radio or wireless communication chip module 131, two 4 channel processing units 132, 134, which may be CODECs, or simple mixers. FIG. 2A shows battery 137 and power circuits with connectors for the two main OBC electrodes 135, 136 and an I/O connector 111 to the peripheral sensors.

Figure 2B:
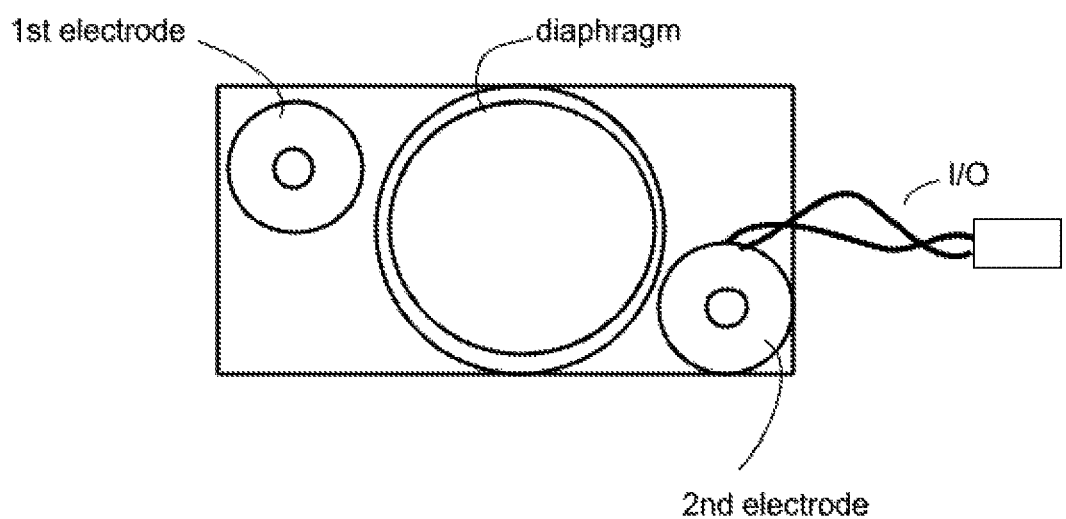
FIG. 2B is a schematic illustration of a top view of a main on-body component of a multi-sensor multi-channel wearable platform for smart remote health monitoring, according to an embodiment.

FIG. 2B is a schematic illustration of a top view of a main on-body component of a multi-sensor multi-channel wearable platform for smart remote health monitoring, according to an embodiment. FIG. 2B shows two electrodes 140, 141 attached to the bottom of the main OBC. These electrodes are preferably ECG and/or EMG capable biosensors. The acoustic sensor diaphragm 142 provides the capability to obtain sound data.

Figure 3:
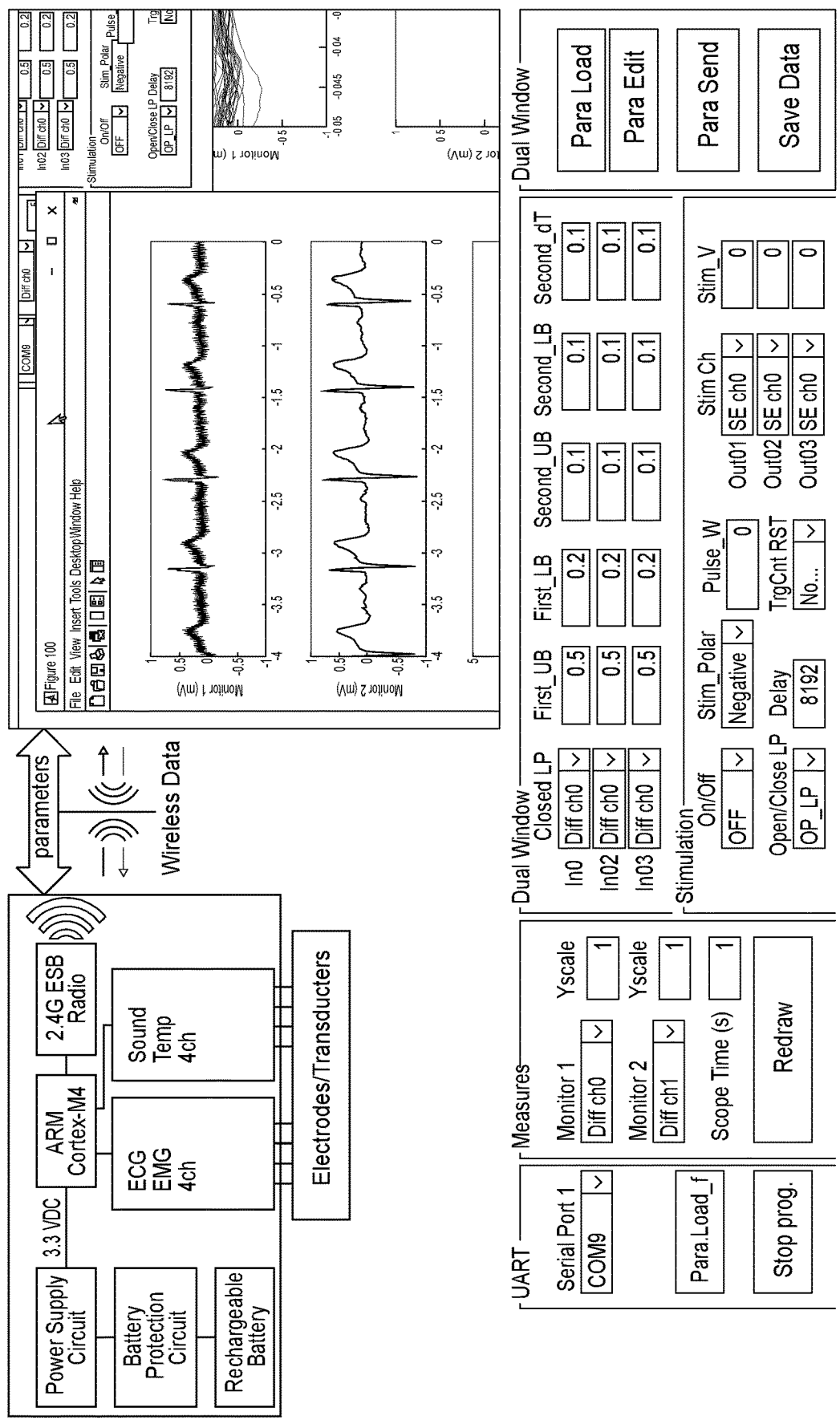
FIG. 3 is a schematic illustration of an embodiment of a main on-body component in wireless communication with a remote health provider server, according to an embodiment.

FIG. 3 is a schematic illustration of an embodiment of a main on-body component in wireless communication with a remote health provider server, according to an embodiment. FIG. 3 shows main OBC with power supply circuit, battery protection circuit, and rechargeable battery, in one embodiment. Main OBC also has an ARM Cortex-M4 processor connected to two four channel modules. A first 4-channel module is dedicated to electrocardiogram (ECG) signal processing and electromyogram (EMG) signal processing, and a second 4-channel module is dedicated to sound sensor and temperature sensor processing, according to an embodiment. Peripheral electrodes or transducers are shown connecting via I/O pins to the main OBC. A wireless communication module is shown as a 2.4 GHz ESB radio. FIG. 3 also shows a duplex wireless connection to a remote external computer capable of graphically displaying sensor output on a display device and displaying sensor values within a user interface that provides data field windows.

Figure 4:
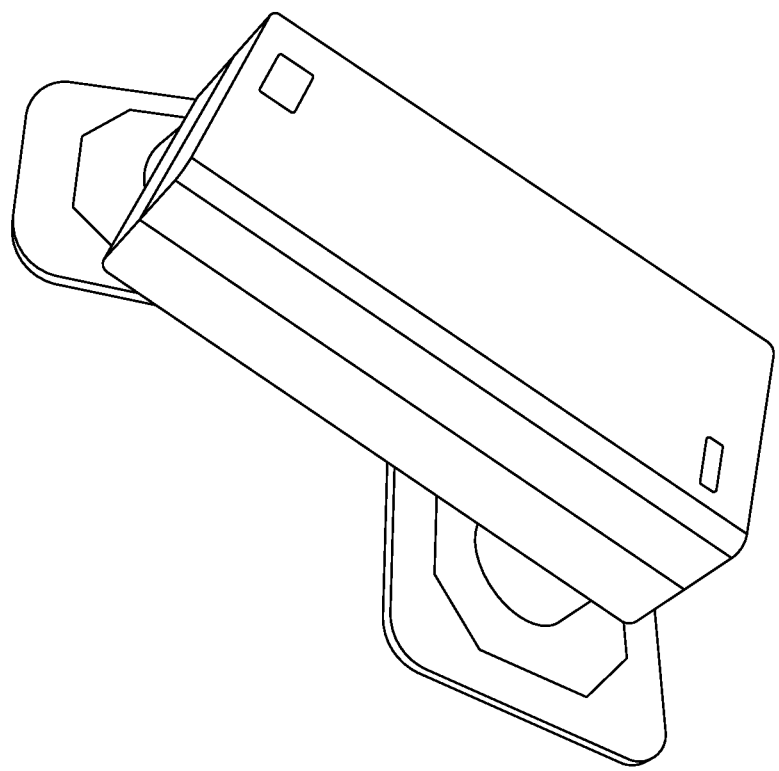
FIG. 4 is a photographic representation of a main on-body component of a multi-sensor multi-channel wearable platform for smart remote health monitoring, according to an embodiment.

FIG. 4 is a photographic representation of a main on-body component of a multi-sensor multi-channel wearable platform for smart remote health monitoring, according to an embodiment. FIG. 4 shows the outer chassis from a perspective view and shows the two (2) biopotential or ECG/EMG sensors/electrodes with adhesive pads for affixing the leads to the, e.g. 5th intercostal space of a patient.

Figure 5:
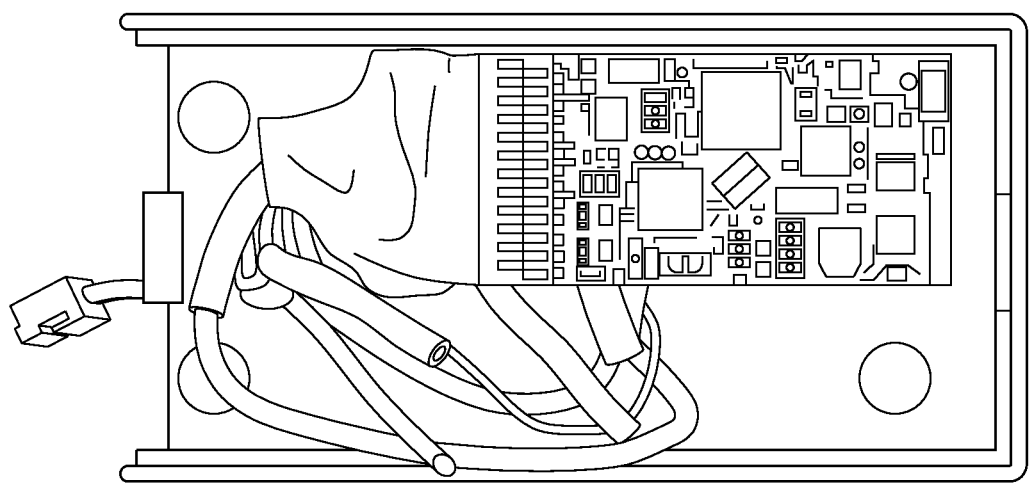
FIG. 5 is a photographic representation of an open—top view of a main on-body component of a multi-sensor multi-channel wearable platform for smart remote health monitoring, according to an embodiment.

FIG. 5 is a photographic representation of an open—top view of a main on-body component of a multi-sensor multi-channel wearable platform for smart remote health monitoring, according to an embodiment. FIG. 5 shows the main on-body component (OBC) having an electronics circuit board with a processor, a radio or wireless communication chip module, two 4 channel processing units, which may be CODECs, or simple mixers. FIG. 2A shows battery and power circuits with connectors for the two main OBC electrodes and an I/O connector to the peripheral sensors.

Figure 6:
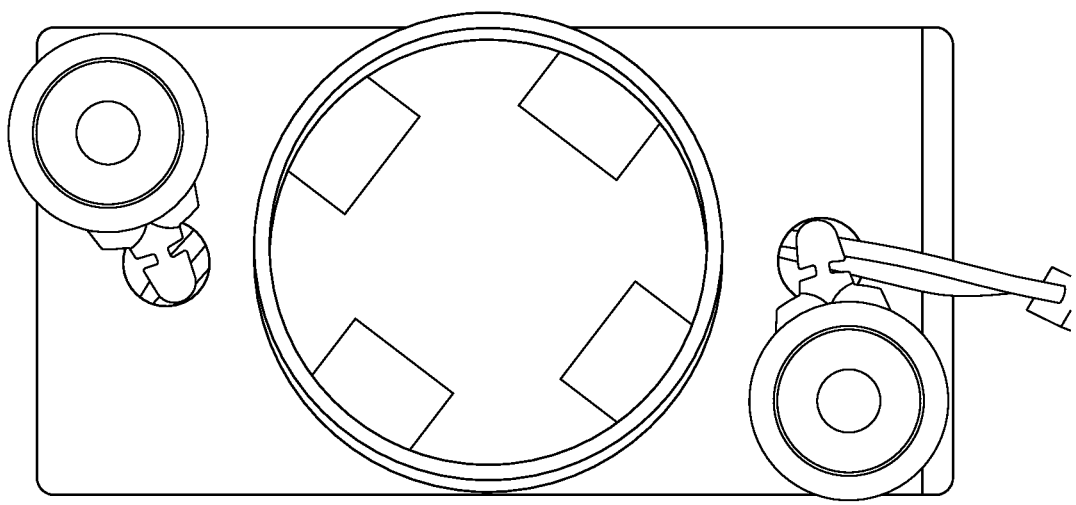
FIG. 6 is a photographic representation of a bottom view of a main on-body component of a multi-sensor multi-channel wearable platform for smart remote health monitoring, according to an embodiment.

FIG. 6 is a photographic representation of a bottom view of a main on-body component of a multi-sensor multi-channel wearable platform for smart remote health monitoring, according to an embodiment. FIG. 6 shows two electrodes attached to the bottom of the main OBC. These electrodes are preferably ECG and/or EMG capable biosensors. The acoustic sensor diaphragm provides the capability to obtain sound data.

Figure 7:
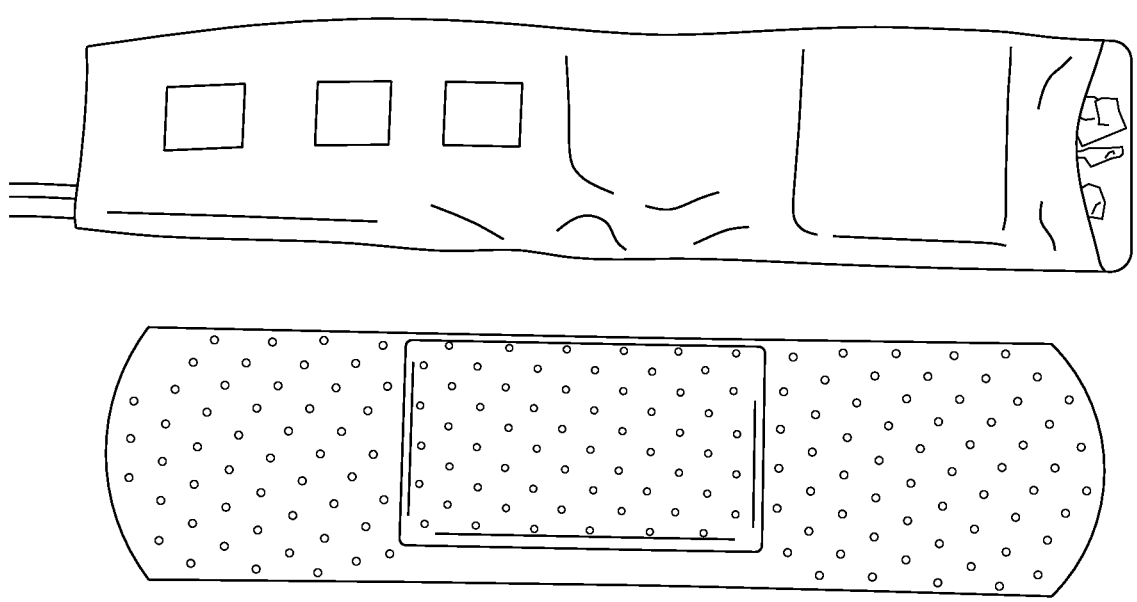
FIG. 7 is a photographic representation of a peripheral on-body component of a multi-sensor multi-channel wearable platform for smart remote health monitoring, shown next to an adhesive bandage for scale, according to an embodiment.

FIG. 7 is a photographic representation of a peripheral on-body component of a multi-sensor multi-channel wearable platform for smart remote health monitoring, shown next to an adhesive bandage for scale, according to an embodiment. FIG. 7 shows peripheral unit (on-body component or OBC) having electronics, with optional processing, and optional wireless communication. Peripheral unit has a transducer array or an array of multiple sensors or electrodes. Peripheral units may connect to the main component by wire or wirelessly. One or more peripheral OBC's may be used to obtain vital sign or patient health data. The peripheral OBC may be a (1) muscle activity (EMG) sensor, (2) acoustic activity (contact microphone) sensor, (3) brain activity (EEG) sensor, (4) eye activity (EOG) sensor, (5) skin temperature sensor, and (6) an x-y-z axis orientation sensor.

Figure 8:
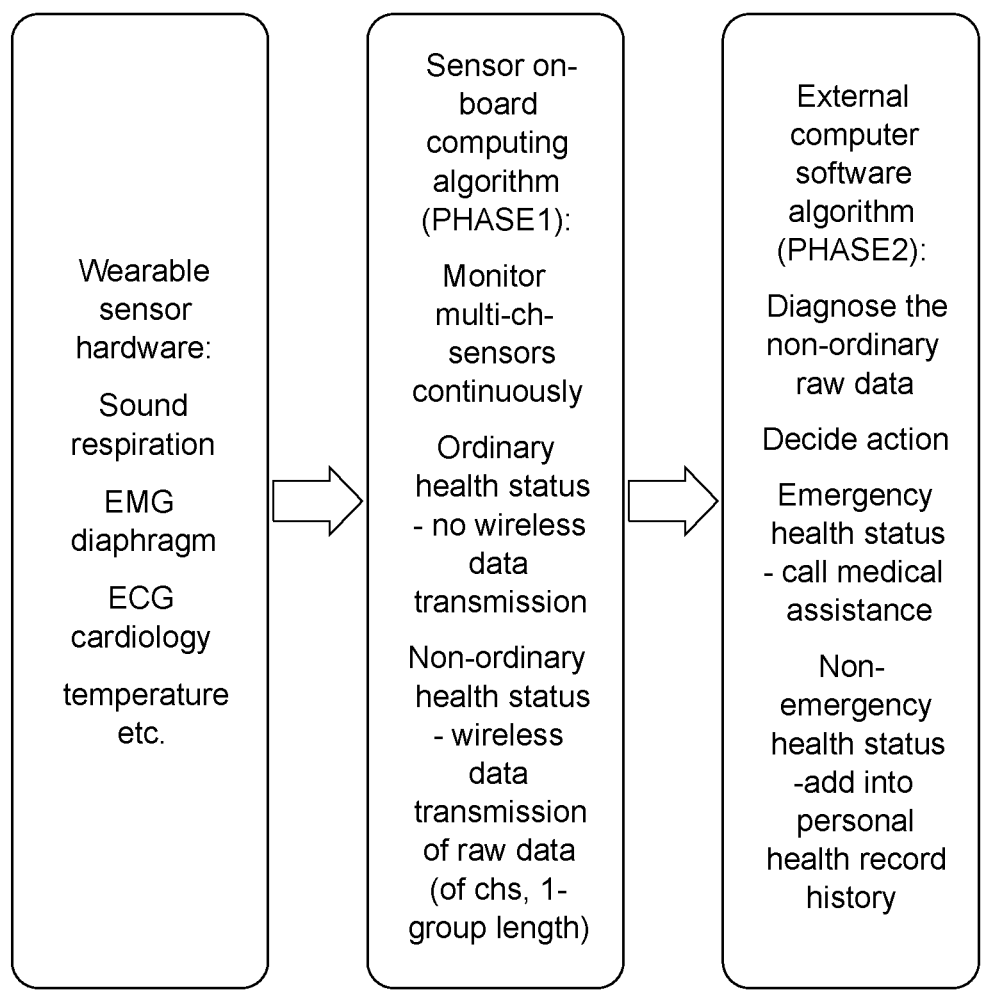
FIG. 8 is a graphic representation of an overview of a multisensor multichannel wearable platform having wearable sensor hardware, with sensors feeding data into on-board processor executing computer program instructions saved to memory to convert the raw data into a matrix of sensor signal patterns made of matrix pixel values derived from subgroup data points, which are themselves derived from the mean and standard deviation values of over 100 sensor data points, sampled continuously over time at a specific frequency, e.g. 4 KHz, and wherein said sensor signal patterns are compared to a baseline sensor signal pattern to derive decision-making factors available to healthcare professional or the patient, according to an embodiment.

FIG. 8 is a graphic representation of an overview of a multisensor multichannel wearable platform having wearable sensor hardware, with sensors feeding data into on-board processor executing computer program instructions saved to memory to convert the raw data into a matrix of sensor signal patterns made of matrix pixel values derived from subgroup data points, which are themselves derived from the mean and standard deviation values of over 100 sensor data points, sampled continuously over time at a specific frequency, e.g. 4 KHz, and wherein said sensor signal patterns are compared to a baseline sensor signal pattern to derive decision-making factors available to healthcare professional or the patient, according to an embodiment.

FIG. 9 is a graphical representation of a two-dimensional sensor signal pattern, signature or ongoing, created from the subgroup data points, according to an embodiment. FIG. 9 shows a two-dimensional "image-like" signature matrix patterns from the sensors. These signature matrix patterns reflect the patient's compressed characteristics per sampling window using the calculated probabilities as pixels of an image frame (See Figures). A real-time sensor data assessment can be conducted by comparing the person's measured signature matrix patterns with the stored patterns. FIG. 9 shows a two-dimensional "image-like" signature matrix pattern from the sensors showing a grid of lower limit X parameters and upper limit X parameters displayed against lower limit Y parameters and upper limit Y parameters. Where a data subgroup forms matrix pixels falling within upper and lower X and upper and lower Y parameters, the pixels are presented using a GREEN color. Where a data subgroup forms matrix pixels falling within the upper and lower X limits, but outside the upper or lower Y limits, the pixel is colored YELLOW. Similarly, where a data subgroup forms matrix pixels falling within the upper and lower Y limits, but outside the upper or lower X limits, the pixel is also colored YELLOW. Special "stop" alerts may be generated when a data subgroup forms matrix pixels falling both below the lower limit of X and Y and are colored RED, or when falling both above the upper limit of X and Y which is also colored RED. In a situation where a data subgroup of patent sensor data forms a matrix pixel falling below the lower limit of X but above the upper limit of Y, or below the lower limit of Y but above the upper limit of X, the pixel is labelled ORANGE.

FIG. 10 is a graphical representation of signal matrix patterns reflecting the visualization of data compression per sampling period or frame, according to an embodiment. FIG. 10 shows how signal matrix patterns are generated during each sample period. FIG. 10 illustrates how heartbeat sounds, lung sounds, ECG, and EMG sensor data may be continuously monitored, either visually by a healthcare provider or automated using machine learning and simple visual detection methods.

FIG. 11 is a graphical representation of a Group that is formed from a series of signature matrix patterns, according to an embodiment. FIG. 11 shows how a time series of signal matrix patterns may also be combined into GROUPS for additional analysis. Trends and comparison against historical values can be used to generate and transmit instruction sets or alerts to the patient and healthcare personnel.

Figure 12:
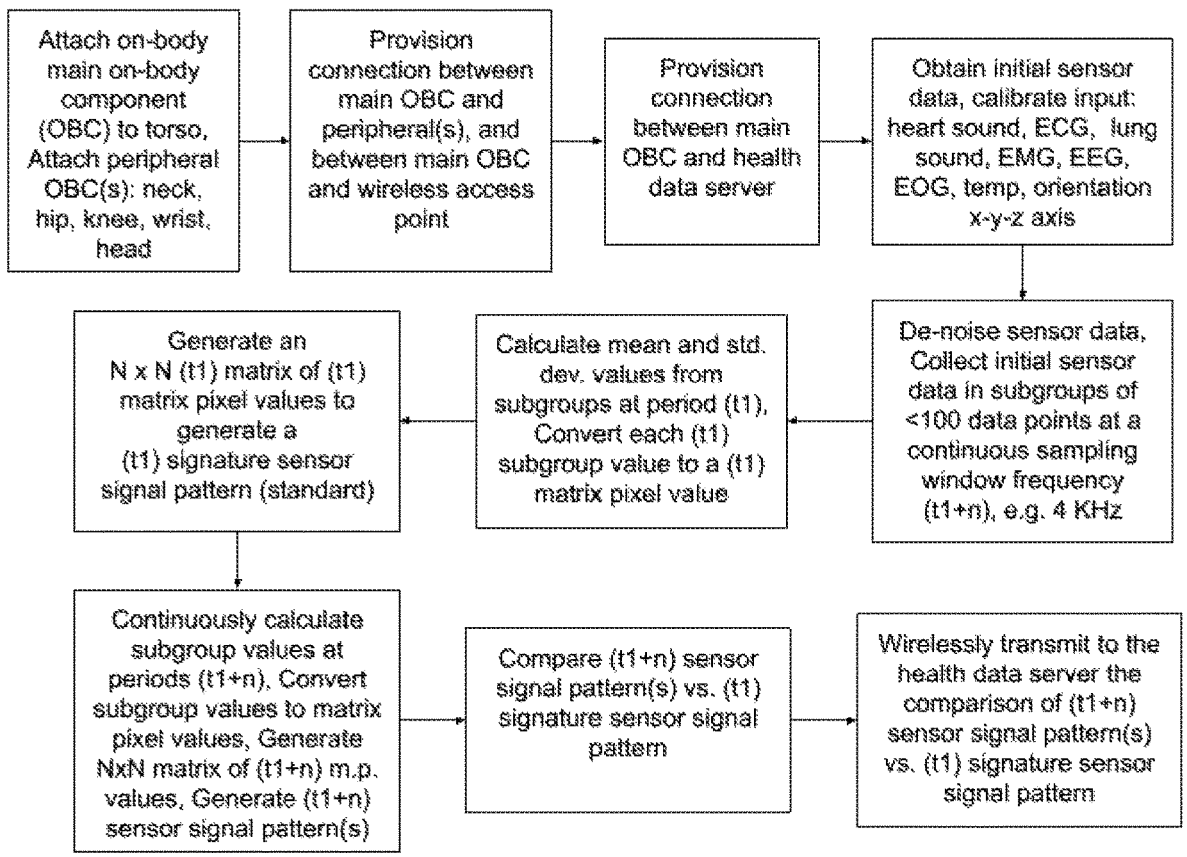
FIG. 12 is a flowchart showing the Phase 1 steps from collecting sensor data to generating matrix patterns performed by the program instructions saved to memory and executable by a processor of the wearable device herein, according to an embodiment.

FIG. 12 is a flowchart showing the Phase 1 steps from collecting sensor data to generating matrix patterns performed by the program instructions saved to memory and executable by a processor of the wearable device herein, according to an embodiment. FIG. 12 shows a series of STEPS performed using computer program instructions saved to memory and executable on a processor. In one non-limiting embodiment, the steps comprise:

1201, 1202, 1203 Provisioning connection between a main on-body component and a peripheral on-body component and provisioning connection between the main on-body component and a health data server computer,

1204 Obtaining initial sensor data from the main and peripheral on-body components, the initial sensor data comprising heart sound, ECG, lung sound, EMG, EEG, EOG, temp, and orientation x-y-z axis,

1205 Collecting initial sensor data in subgroups of <100 data points at a continuous sampling window frequency (t1+n), said frequency selected from 4 KHz, 1-10 KHz, 2 KHz, and 1-20 KHz,

1206 Calculating mean and standard deviation values from subgroups at period (t1), and Converting each (t1) subgroup value to a (t1) matrix pixel value,

1207 Generating an N×N (t1) matrix of (t1) matrix pixel values to generate a (t1) signature sensor signal pattern (standard),

1208 Continuously calculating subgroup values at periods (t1+n), and Converting subgroup values to matrix pixel values, Generating an N×N matrix of (t1+n) matrix pixel values, and Generating a (t1+n) sensor signal pattern(s) from said (t1+n) matrix pixel values,

1209 Comparing (t1+n) sensor signal pattern(s) against the (t1) signature sensor signal pattern, and

1210 Wirelessly transmitting to the health data server the comparison of (t1+n) sensor signal pattern(s) against the (t1) signature sensor signal pattern.

Figure 13:
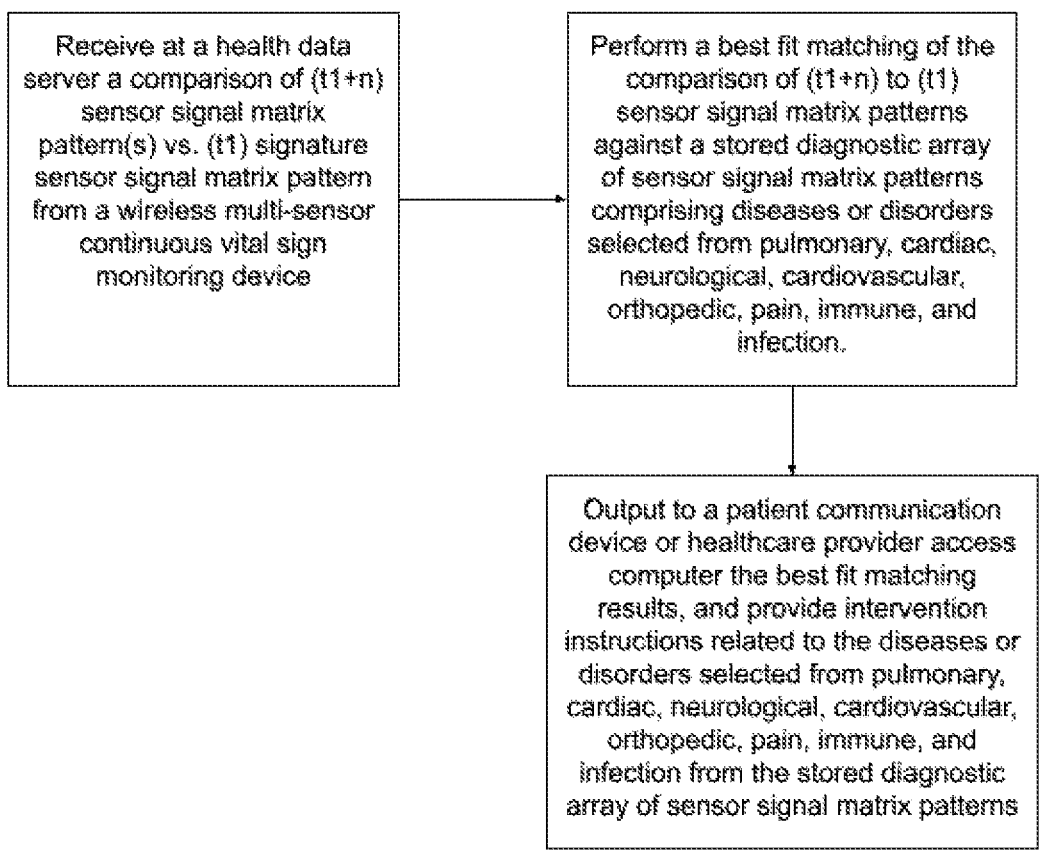
FIG. 13 is a flowchart showing the Phase 2 steps of matching signature patterns to specific pathologies to generate patient instructions performed by the program instructions saved to memory and executable by a processor of the system herein, according to an embodiment.

FIG. 13 is a flowchart showing the Phase 2 steps of matching signature patterns to specific pathologies to generate patient instructions performed by the program instructions saved to memory and executable by a processor of the system herein, according to an embodiment. FIG. 13 shows a series of ADDITIONAL STEPS performed using computer program instructions saved to memory and executable on a processor. In one non-limiting embodiment, the ADDITIONAL STEPS comprise:

1301 Receiving at a health data server a comparison of (t1+n) sensor signal matrix pattern(s) against the (t1) signature sensor signal matrix pattern from a wireless multi-sensor continuous vital sign monitoring device,

1302 Performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection, and

Figure 14:
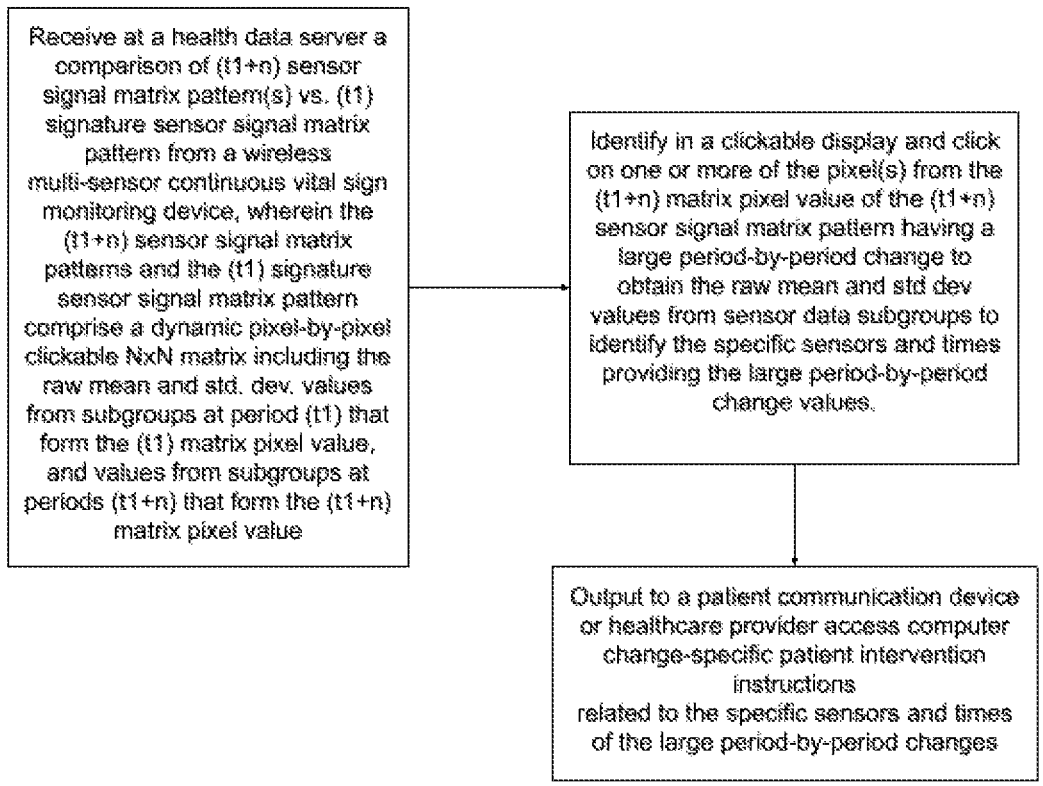
FIG. 14 is a flowchart showing the Phase 2 steps of providing a click-thru feature to be able to click on a specific pixel or set of pixels responsible for the look of a given signal matrix pattern to be able to access the raw sensor data, an raw subgroup data responsible for generating the pixel or set of pixels, and to generate patient instructions relating to the raw sensor data causing a specific pixel or set of pixels, according to an embodiment.

1303 Outputting to a patient communication device or healthcare provider access computer the best fit matching results, and provide intervention instructions related to the diseases or disorders selected from pulmonary, cardiac, neurological, cardiovascular, orthopedic, pain, immune, and infection from the stored diagnostic array of sensor signal matrix patterns FIG. 14 is a flowchart showing the Phase 2 steps of providing a click-thru feature to be able to click on a specific pixel or set of pixels responsible for the look of a given signal matrix pattern to be able to access the raw sensor data, an raw subgroup data responsible for generating the pixel or set of pixels, and to generate patient instructions relating to the raw sensor data causing a specific pixel or set of pixels, according to an embodiment. FIG. 14 shows a series of ADDITIONAL STEPS performed using computer program instructions saved to memory and executable on a processor. In one non-limiting embodiment, the ADDITIONAL STEPS comprise:

1401 Receiving at a health data server a comparison of (t1+n) sensor signal matrix pattern(s) against the (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and std. dev. values from subgroups at period (t1) that form the (t1) matrix pixel value, and values from subgroups at periods (t1+n) that form the (t1+n) matrix pixel value,

1402 Identifying in a clickable display and clicking on one or more of the pixel(s) from the (t1+n) matrix pixel value of the (t1+n) sensor signal matrix pattern having a large period-by-period change to obtain the raw mean and standard deviation values from sensor data subgroups to identify the specific sensors and times providing the large period-by-period change values, and

1403 Outputting to a patient communication device or healthcare provider access computer change-specific patient intervention instructions related to the specific sensors and times of the large period-by-period changes.

Figure 15:
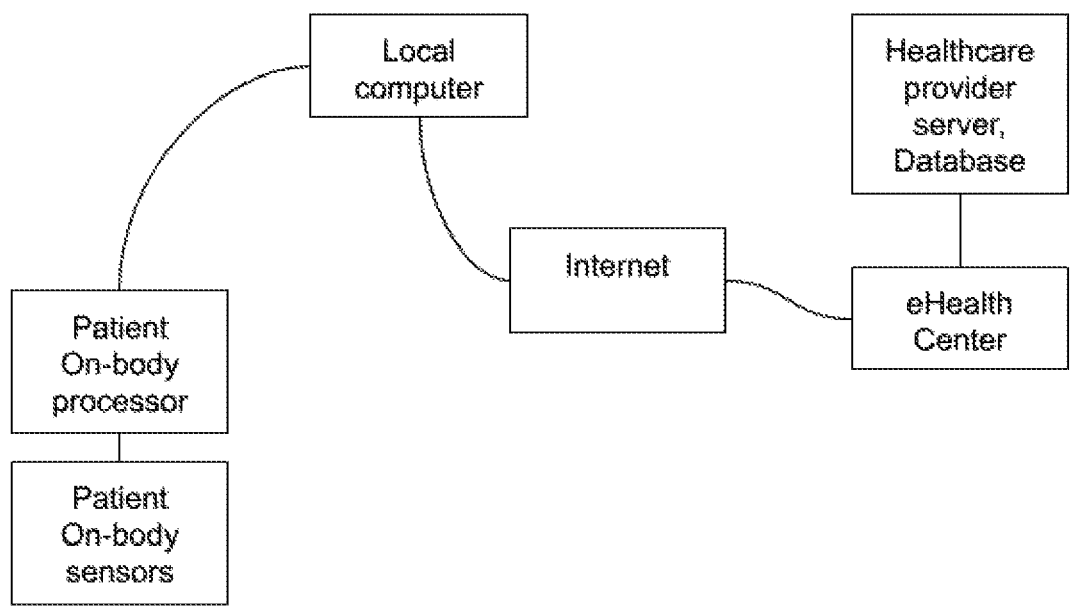
FIG. 15 is an illustration of a multi-sensor multi-channel wearable platform for smart remote health monitoring showing the connection among the on-body device, the local internet access, and the healthcare provider server and database, according to an embodiment

FIG. 15 is an illustration of a multi-sensor multi-channel wearable platform for smart remote health monitoring 1501, 1502 showing the connection among the on-body device 1501, 1502, the local internet access 1503, 1504, and the healthcare provider server and database 1505, 1506, according to an embodiment.

Figure 16A:
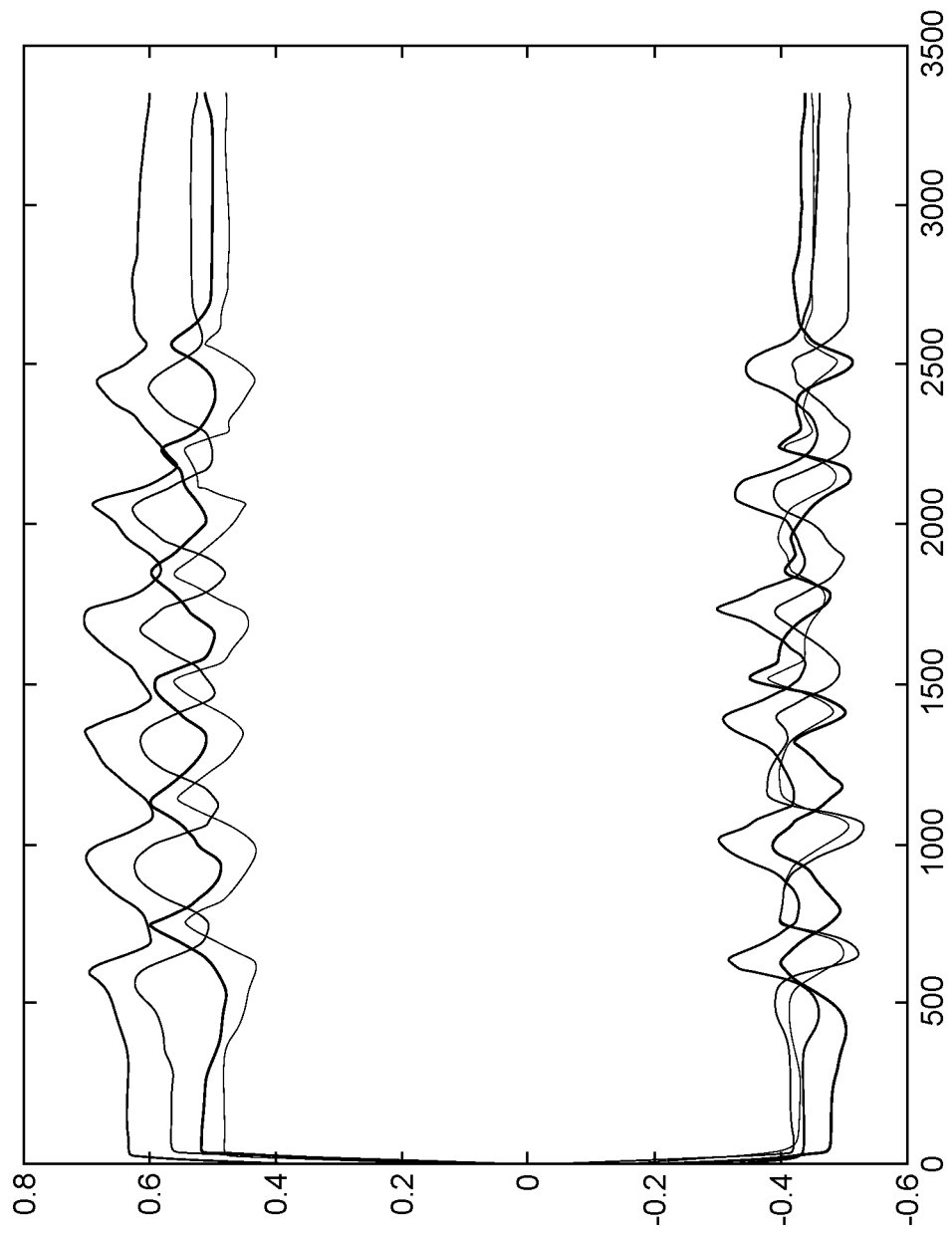
FIG. 16A is a graph showing an example of raw sensor signals from a set of two IMUs located on hip and knee.
Figure 16B:
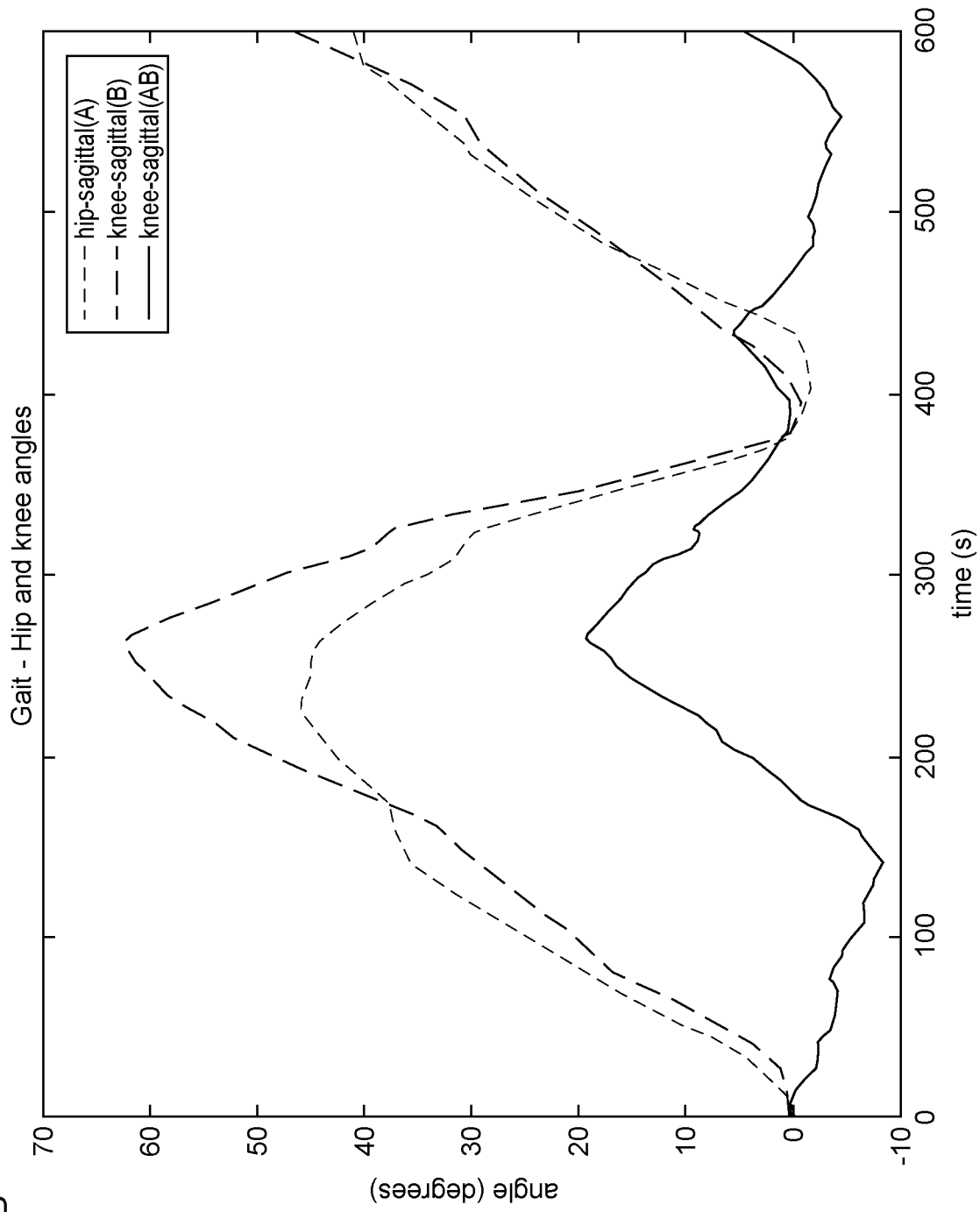
FIG. 16B is a graph of angle over time-associated with abnormal walking, hemiplegic gait, according to an embodiment.

FIG. 16A is a graph showing an example of raw sensor signals from a set of two IMUs located on hip and knee. FIG. 16B is a graph of angle over time-associated with abnormal walking, hemiplegic gait, according to an embodiment.

Figure 17A:
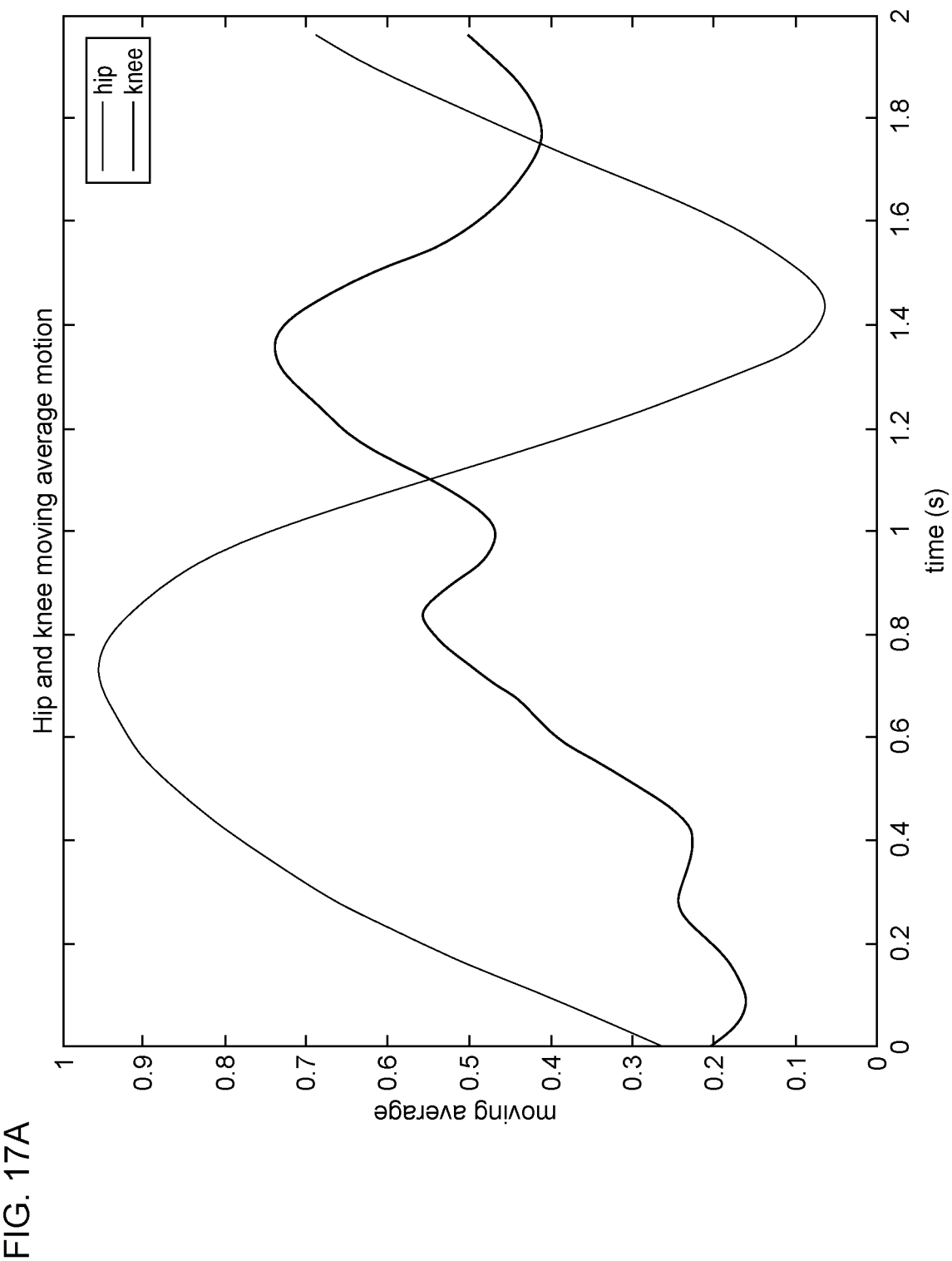
FIG. 17A is a graph of moving average over time showing an example of calculated hip and knee joint angle patterns from a period of a 2.5 second data packet, according to an embodiment.
Figure 17B:
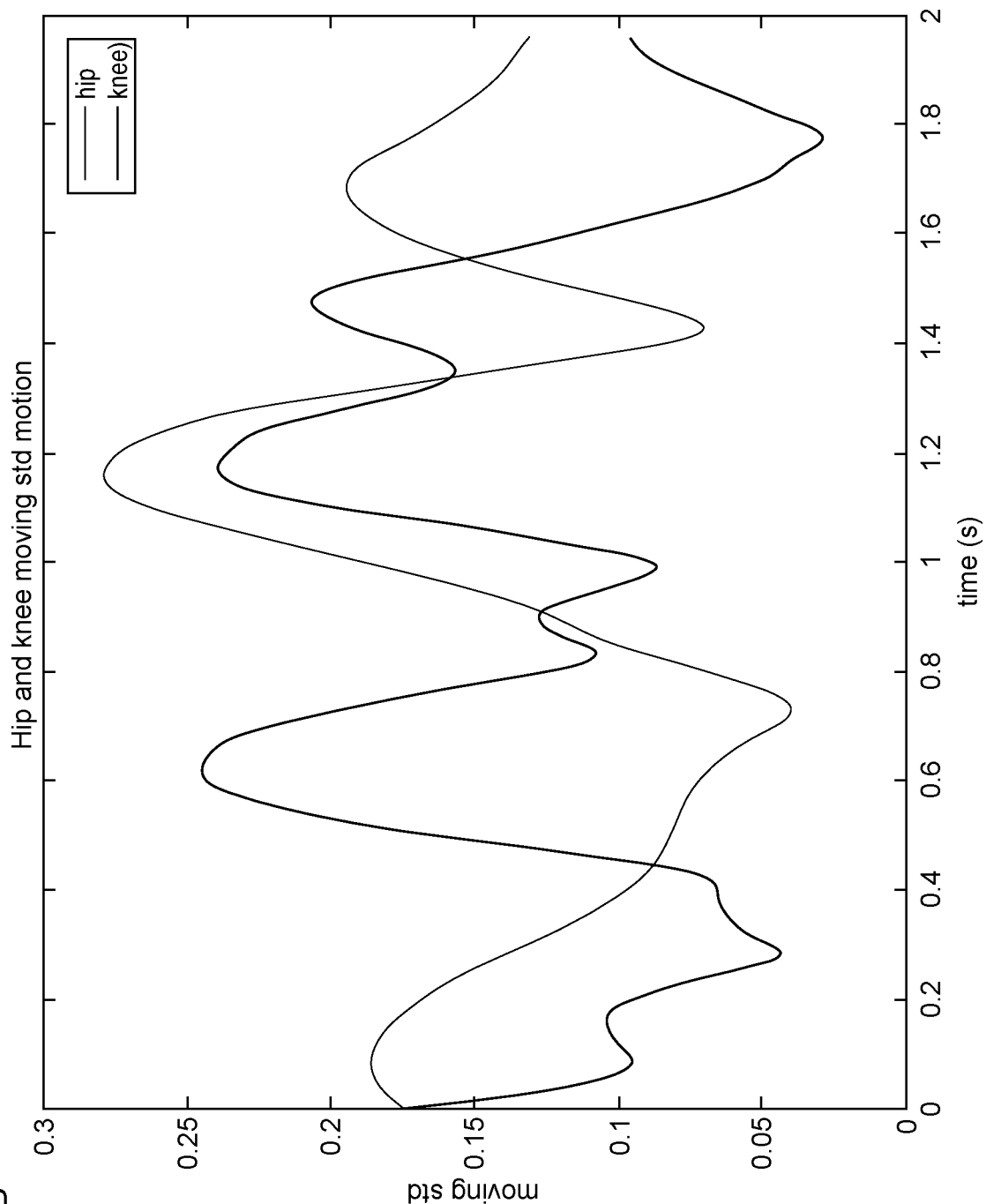
FIG. 17B is a graph of moving standard deviation over time.

FIG. 17A is a graph of moving average over time showing an example of calculated hip and knee joint angle patterns from a period of a 2.5 second data packet, according to an embodiment. FIG. 17B is a graph of a moving standard deviation over time.

Figure 18A:
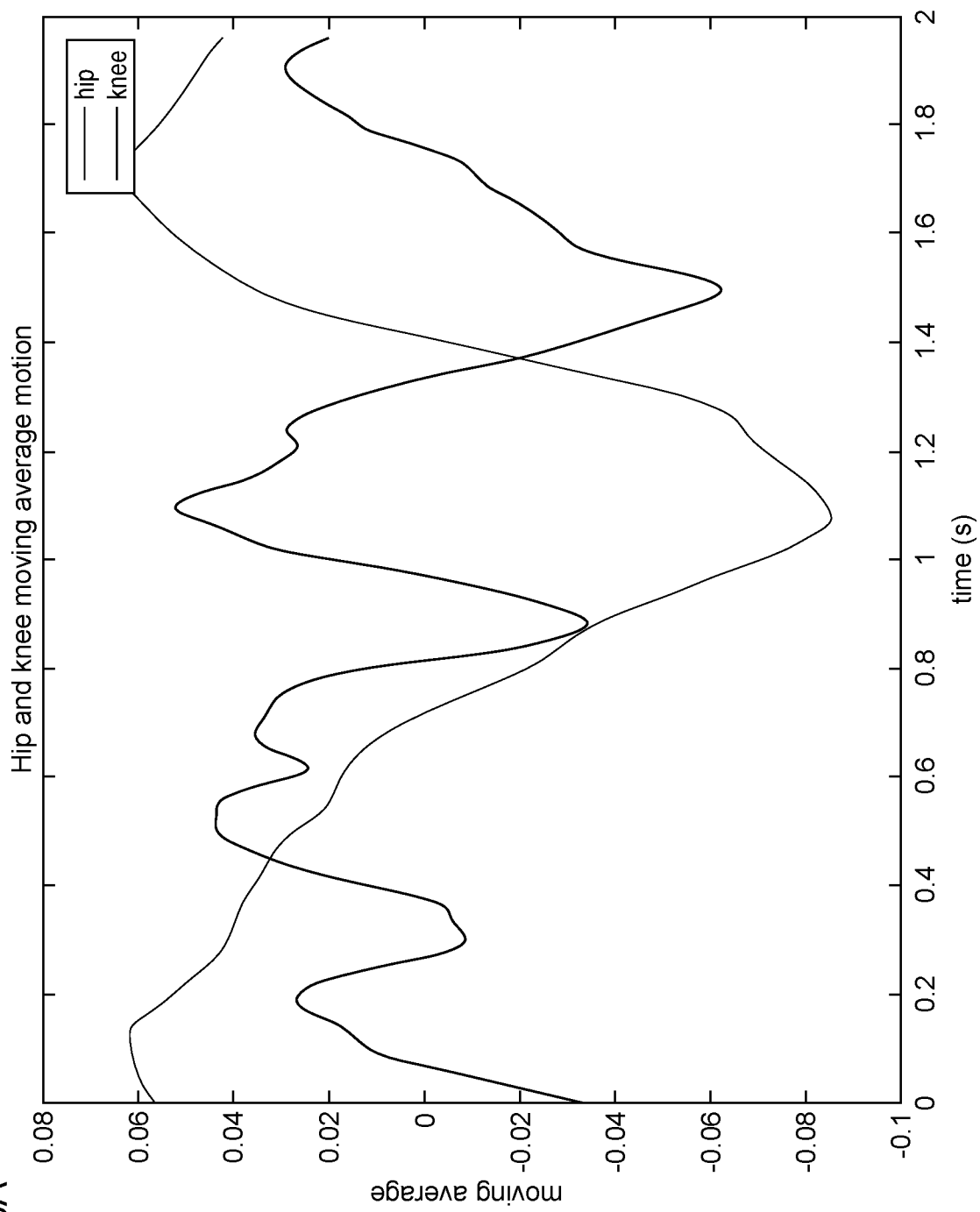
FIG. 18A is a graph showing an example of a moving average from data in the packet for filtering-associated with abnormal walking, hemiplegic gait, according to an embodiment.

FIG. 18A is a graph showing an example of a moving average from data in the packet for filtering-associated with abnormal walking, hemiplegic gait, according to an embodiment.

Figure 18B:
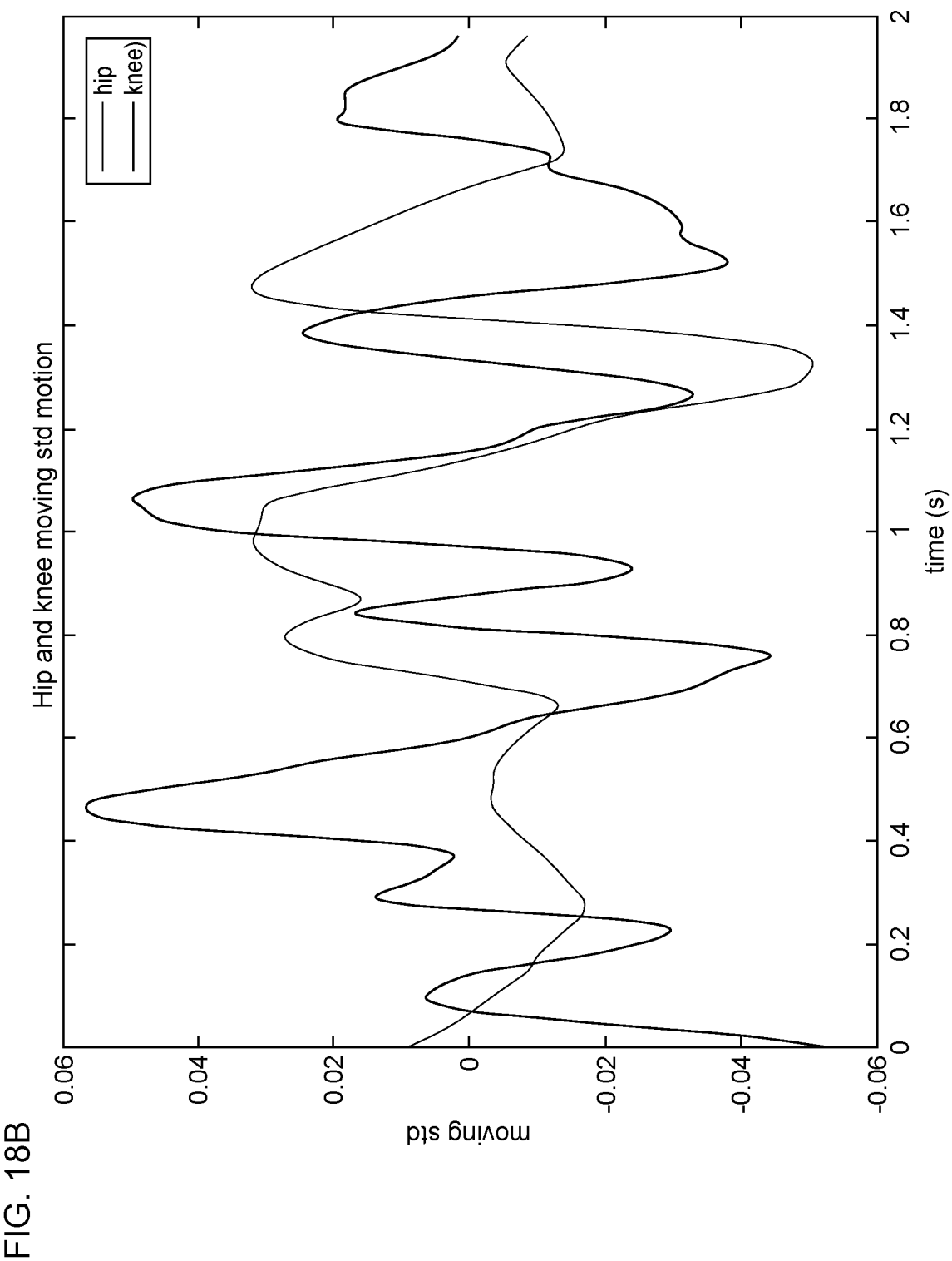
FIG. 18B is a graph showing an example of a moving standard deviation from data in the packet for filtering—associated with abnormal walking, hemiplegic gait, according to an embodiment.

FIG. 18B is a graph showing an example of a moving standard deviation from data in the packet for filtering-associated with abnormal walking, hemiplegic gait, according to an embodiment.

Figure 19:
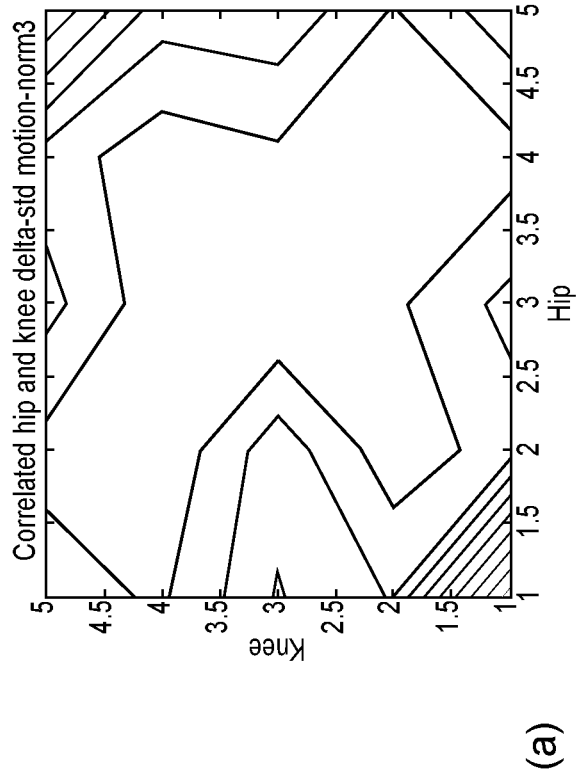
FIG. 19 is a comparison of graphs showing an example of the calculated signature matrices and the associated image plots for average (a) and standard deviation (b) from data in the packet—associated with abnormal walking—hemiplegic gait, according to an embodiment.
Figure 19:
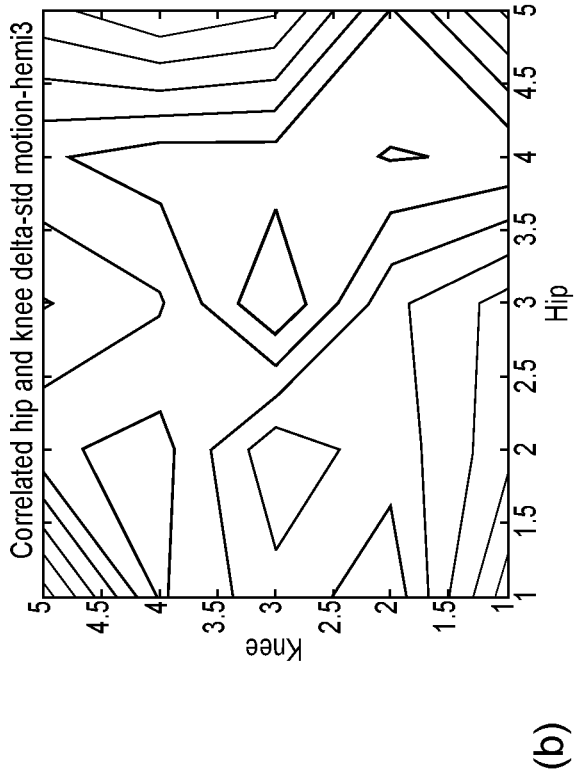

FIG. 19 is a comparison of graphs showing an example of the calculated signature matrices and the associated image plots for average (a) and standard deviation (b) from data in the packet-associated with abnormal walking-hemiplegic gait, according to an embodiment. FIG. 19 shows examples of an alternative display of signal matrix patterns.

Figure 20:
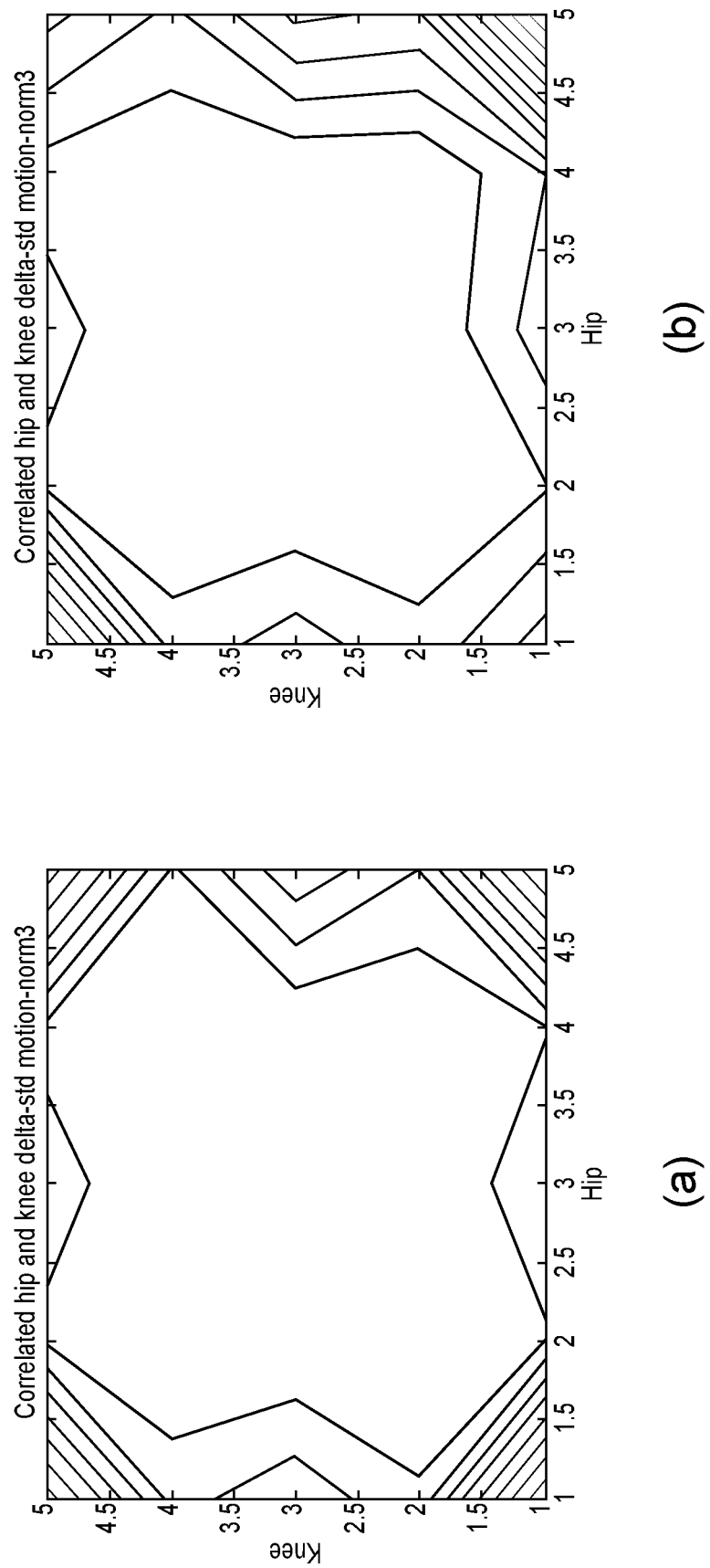
FIG. 20 is a comparison of graphs showing an example of the calculated signature matrices and the associated image plots for average (a) and standard deviation (b) from data in the packet—associated with normal walking, according to an embodiment.

FIG. 20 is a comparison of graphs showing an example of the calculated signature matrices and the associated image plots for average (a) and standard deviation (b) from data in the packet-associated with normal walking, according to an embodiment. FIG. 20 shows examples of an alternative display of signal matrix patterns.

Figure 21:
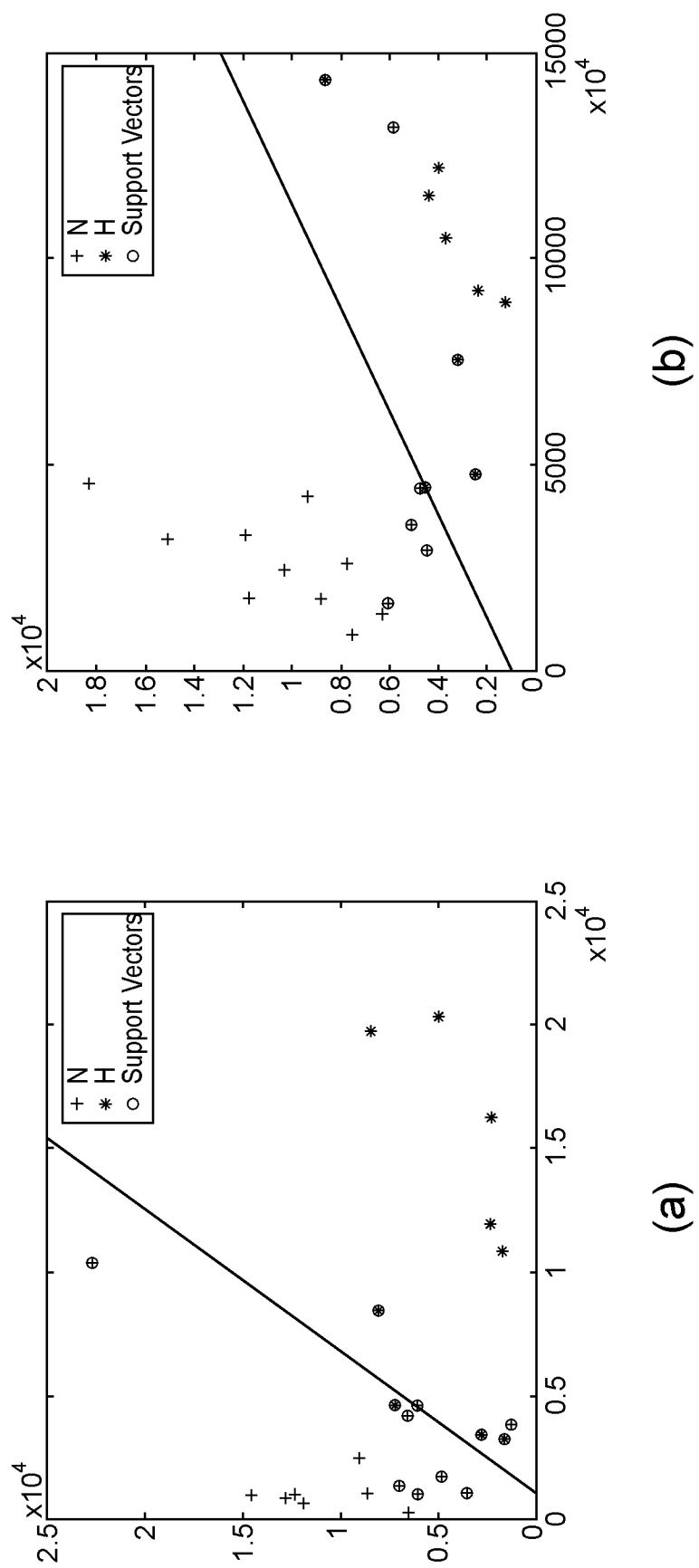
FIG. 21 is a comparison of graphs showing an example of the calculated hyperplane boundary from a SVM (smart vector machine) machine-learning algorithm with training data sets for average (a) and standard deviation (b)— associated with normal vs. abnormal walking, according to an embodiment.

FIG. 21 is a comparison of graphs showing an example of the calculated hyperplane boundary from a SVM (smart vector machine) machine-learning algorithm with training data sets for average (a) and standard deviation (b)—associated with normal vs. abnormal walking, according to an embodiment.

Figure 22:
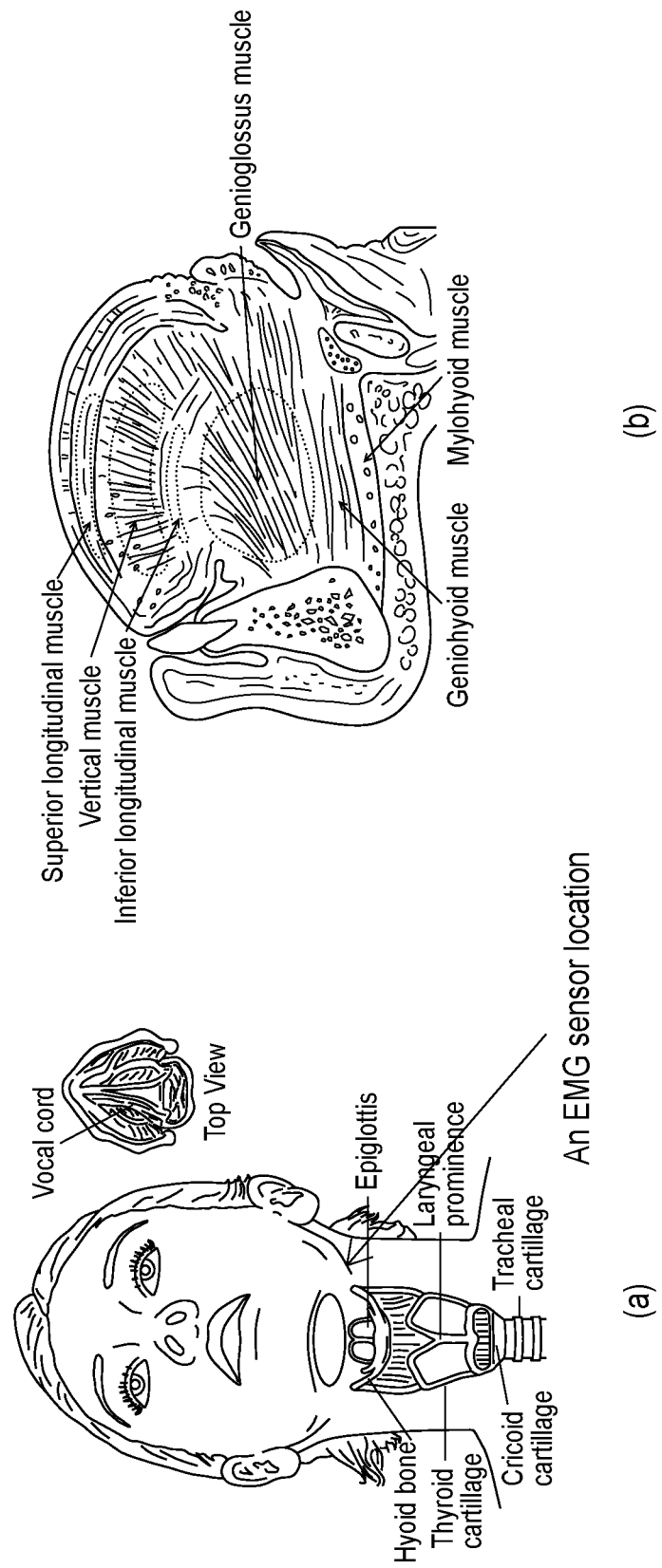
FIG. 22 is an illustration of a patient's anatomy showing one example of an EMG sensor location for obtaining sensor data on tongue and related activity—associated with sleep apnea, according to an embodiment.

FIG. 22 is an illustration of a patient's anatomy showing one example of an EMG sensor location for obtaining sensor data on tongue and related activity—associated with sleep apnea, according to an embodiment.

Figure 23:
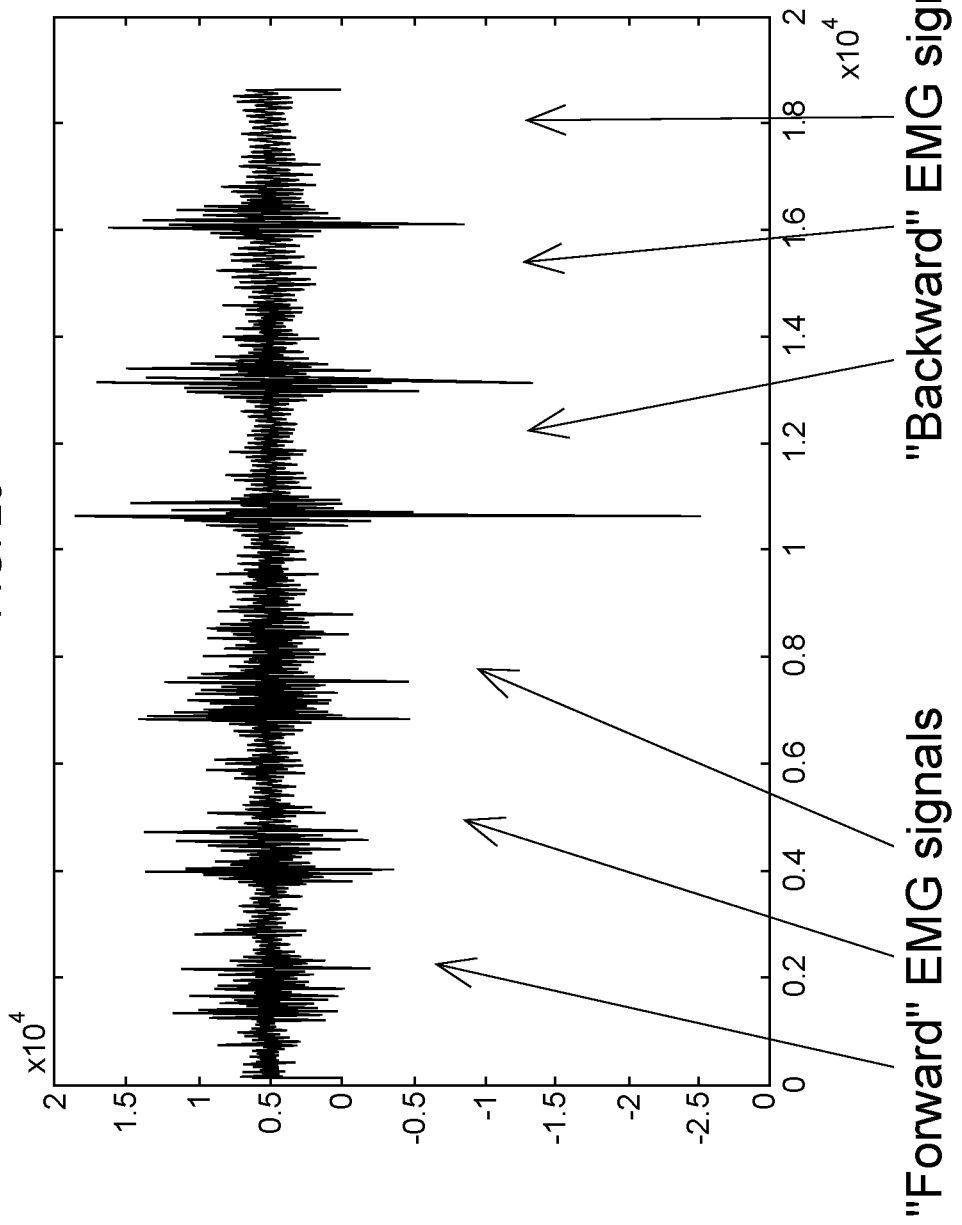
FIG. 23 is an illustration of a graph showing Forward EMG signal and Backward EMG signals, according to an embodiment.

FIG. 23 is an illustration of a graph showing Forward EMG signal and Backward EMG signals, according to an embodiment.

Figure 24:
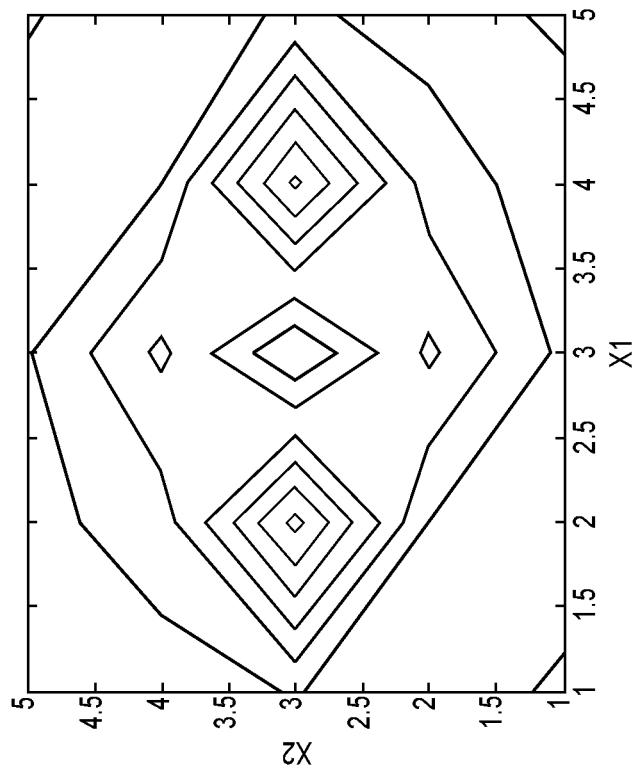
FIG. 24 is a comparison of graphs showing image plots showing Forward EMG signal and Backward EMG signals, according to an embodiment.
Figure 24:
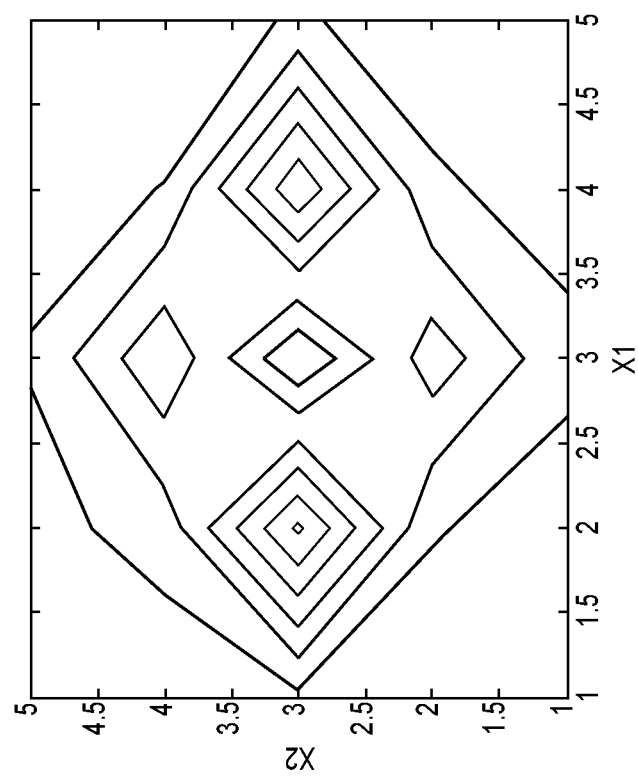

FIG. 24 is a comparison of graphs showing image plots showing Forward EMG signal and Backward EMG signals, according to an embodiment. FIG. 24 shows examples of an alternative display of signal matrix patterns.

Figure 25:
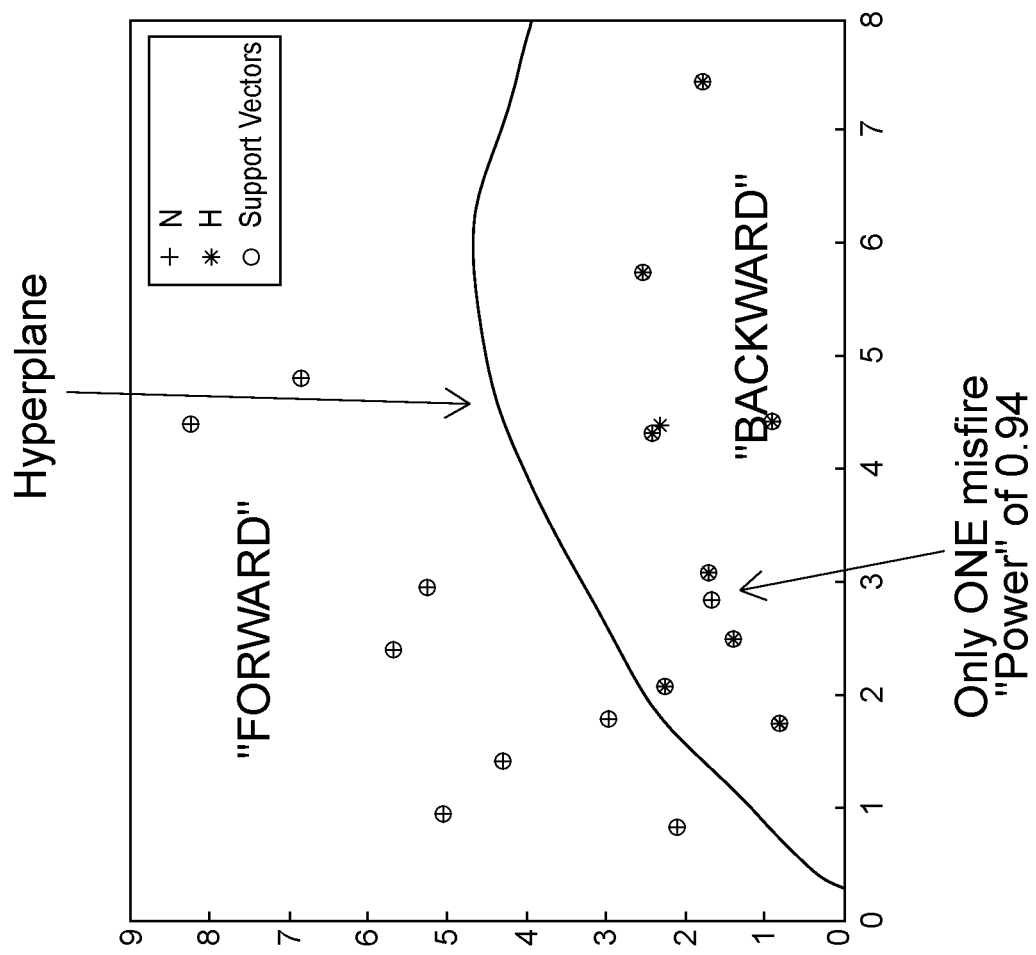
FIG. 25 is a graph showing a no-sound communication using an EMG physiological sensor signals to detect a tongue muscle motions: (a) EMG sensor location; (b) tongue muscle; (c) "Forward" EMG signals; (d) "Backward" EMG signals; (e) "Forward" signature matrix image plot; (f) "Backward" signature matrix image plot; (g) SVM hyperplane boundary between "Forward" vs. "Backward", according to an embodiment.

FIG. 25 is a graph showing a no-sound communication using an EMG physiological sensor signals to detect a tongue muscle motions: (a) EMG sensor location; (b) tongue muscle; (c) "Forward" EMG signals; (d) "Backward" EMG signals; (e) "Forward" signature matrix image plot; (f) "Backward" signature matrix image plot; (g) SVM hyperplane boundary between "Forward" vs. "Backward", according to an embodiment.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

The invention claimed is:

1. A computer implemented system for continuous monitoring of patient health data, comprising:
 a main on-body component configured to be attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter;
 a peripheral on-body component configured to be attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module;
 a local wireless access component having an internet connection;
 a health data server computer having a database and having program instructions saved to memory and executable by a processor for receiving, manipulating, storing, and transmitting patient health data;
 computer program instructions saved to memory and executable by the main on-body component microprocessor for performing the following steps in order:
 provisioning connection between the main on-body component and the peripheral on-body component and provisioning connection between the main on-body component and the health data server computer;
 obtaining initial sensor data from the main and peripheral on-body components, the initial sensor data comprising heart sound, ECG, lung sound, EMG, EEG, EOG, temperature, and orientation x-y-z axis;
 collecting initial sensor data in subgroups of <100 data points at a continuous sampling window frequency (t1+n), said frequency selected from the group consisting of 4 KHz, 1-10 KHz, 2 KHz, and 1-20 KHz;
 calculating mean and standard deviation values from subgroups at period t1, and converting each (t1) subgroup value to a (t1) matrix pixel value;
 generating an N×N (t1) matrix of matrix pixel values to generate a (t1) signature sensor signal pattern;
 continuously calculating subgroup values at periods t1+n, and converting subgroup values to matrix pixel values;
 generating an N×N matrix of (t1+n) matrix pixel values, and generating a (t1+n) sensor signal pattern(s) from said (t1+n) matrix pixel values;
 comparing (t1+n) sensor signal pattern(s) against the (t1) signature sensor signal pattern; and
 wirelessly transmitting to the health data server the comparison of (t1+n) sensor signal pattern against the (t1) signature sensor signal pattern.

2. The computer implemented system of claim 1, wherein the computer program instructions readable by the main on-body component microprocessor stored to memory are configured to perform the following additional steps in order:
 receiving at the health data server a comparison of (t1+n) sensor signal matrix pattern(s) against the (t1) signature sensor signal matrix pattern from a wireless multi-sensor continuous vital sign monitoring device;

performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection; and outputting to a patient communication device or healthcare provider access computer the best fit matching results, and providing intervention instructions related to the diseases or disorders selected from the group consisting of pulmonary, cardiac, neurological, cardiovascular, orthopedic, pain, immune, and infection from the stored diagnostic array of sensor signal matrix patterns.

3. The computer implemented system of claim 1, wherein the computer program instructions readable by the main on-body component microprocessor stored to memory are configured to perform the following additional steps in order:

receive at a health data server a comparison of (t1+n) sensor signal matrix pattern(s) vs. (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and standard deviation values from subgroups at period that form the (t1) matrix pixel value, and values from subgroups at periods t1+n that form the (t1+n) matrix pixel value;

identify in a clickable display and click on one or more of the pixel(s) from the (t1+n) matrix pixel value of the (t1+n) sensor signal matrix pattern having a large period-by-period change to obtain the raw mean and standard deviation values from sensor data subgroups to identify the specific sensors and times providing the large period-by-period change values; and output to a patient communication device or healthcare provider access computer change-specific patient intervention instructions related to the specific sensors and times of the large period-by-period changes.

4. The computer implemented system of claim 1, wherein the peripheral on-body-component is configured to be attached to a patient at a location selected from the group consisting of: hip, knee, neck, arm, wrist, forehead, occipital region, sternum, and shoulder.

5. The computer implemented system of claim 1, comprising two or more peripheral on-body-components, wherein the two or more peripheral on-body-components are configured to be attached to a patient at different locations selected from the group consisting of: hip, knee, neck, arm, wrist, forehead, occipital region, sternum, and shoulder.

6. A non-transitory computer readable medium having program instructions embodied therewith for continuous monitoring of patient health data, said program instructions comprising the steps:

provisioning connection between a main on-body component and a peripheral on-body component and provisioning connection between the main on-body component and a health data server computer, wherein the main on-body component is configured to be attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter, wherein the peripheral on-body component attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module;

connecting the main on-body component to a local wireless access component having an internet connection, and connecting the main on-body component to a health data server computer having a database and having program instructions saved to memory and executable by a processor for receiving, manipulating, storing, and transmitting patient health data;

obtaining initial sensor data from the main and peripheral on-body components, the initial sensor data comprising heart sound, ECG, lung sound, EMG, EEG, EOG, temperature, and orientation x-y-z axis;

collecting initial sensor data in subgroups of <100 data points at a continuous sampling window frequency (t1+n), said frequency selected from the group consisting of 4 KHz, 1-10 KHz, 2 KHz, and 1-20 KHz;

calculating mean and standard deviation values from subgroups at period (t1), and converting each (t1) subgroup value to a (t1) matrix pixel value;

generating an N×N (t1) matrix of (t1) matrix pixel values to generate a (t1) signature sensor signal pattern;

continuously calculating subgroup values at periods t1+n, and converting subgroup values to matrix pixel values;

generating an N×N matrix of (t1+n) matrix pixel values, and generating a (t1+n) sensor signal pattern(s) from said (t1+n) matrix pixel values;

comparing (t1+n) sensor signal pattern(s) against the (t1) signature sensor signal pattern, and wirelessly transmitting to the health data server the comparison of (t1+n) sensor signal pattern(s) against the (t1) signature sensor signal pattern.

7. The non-transitory computer readable medium of claim 6, wherein the computer program instructions perform the following additional steps in order:

receiving at a health data server a comparison of (t1+n) sensor signal matrix pattern(s) against the (t1) signature sensor signal matrix pattern from a wireless multi-sensor continuous vital sign monitoring device;

performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection; and outputting to a patient communication device or healthcare provider access computer the best fit matching results, and providing intervention instructions related to the diseases or disorders selected from the group consisting of pulmonary, cardiac, neurological, cardiovascular, orthopedic, pain, immune, and infection from the stored diagnostic array of sensor signal matrix patterns.

8. The non-transitory computer readable medium of claim 6, wherein the computer program instructions perform the following additional steps in order:
   receiving at a health data server a comparison of (t1+n) sensor signal matrix pattern(s) against the (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and standard deviation values from subgroups at period (t1) that form the (t1) matrix pixel value, and values from subgroups at periods (t1+n) that form the (t1+n) matrix pixel value;
   identifying in a clickable display and clicking on one or more of the pixel(s) from the (t1+n) matrix pixel value of the (t1+n) sensor signal matrix pattern having a large period-by-period change to obtain the raw mean and standard deviation values from sensor data subgroups to identify the specific sensors and times providing the large period-by-period change values; and
   outputting to a patient communication device or healthcare provider access computer change-specific patient intervention instructions related to the specific sensors and times of the large period-by-period changes.

9. The non-transitory computer readable medium of claim 6, wherein the peripheral on-body-component is configured to be attached to a patient at a location selected from: hip, knee, neck, arm, wrist, forehead, occipital region, sternum, and shoulder.

10. The non-transitory computer readable medium of claim 6, wherein the peripheral on-body component comprising two or more peripheral on-body-components, wherein the two or more peripheral on-body-components are configured to be attached to a patient at different locations selected from: hip, knee, neck, arm, wrist, forehead, occipital region, sternum, and shoulder.

11. A computer implemented method for continuous monitoring of patient health data, comprising:
   providing a main on-body component attached to the patient, the main on-body component having a housing, a first electrode sensor, a second electrode sensor, an acoustic diaphragm sensor, an electronics module within the housing, the electronics module having in operative communication a microprocessor, memory, a first four-channel module, a second four-channel module, a power supply, a wireless communication module including an antenna, and a main-to-peripheral connection I/O module including an amplifier, a filter, and a converter;
   providing a peripheral on-body component attached to the patient, the peripheral on-body component having a peripheral housing, a peripheral electronics module within the peripheral housing, the peripheral electronics module having in operative communication a third electrode sensor, a fourth electrode sensor, and a peripheral-to-main connection I/O module,
   providing a local wireless access component having an internet connection, Providing a health data server computer having a database and having program instructions saved to memory and executable by a processor for receiving, manipulating, storing, and transmitting patient health data;
   providing computer program instructions saved to memory and executable by the main on-body component microprocessor and performing therewith the following steps in order:
      provisioning connection between a main on-body component and a peripheral on-body component and provisioning connection between the main on-body component and a health data server computer;
      obtaining initial sensor data from the main and peripheral on-body components, the initial sensor data comprising heart sound, ECG, lung sound, EMG, EEG, EOG, temperature, and orientation x-y-z axis;
      collecting initial sensor data in subgroups of <100 data points at a continuous sampling window frequency (t1+n), said frequency selected from the group consisting of 4 KHz, 1-10 KHz, 2 KHz, and 1-20 KHz;
      calculating mean and standard deviation values from subgroups at period (t1); and
      converting each (t1) subgroup value to a (t1) matrix pixel value, Generating an N×N (t1) matrix of (t1) matrix pixel values to generate a (t1) signature sensor signal pattern (standard);
      continuously calculating subgroup values at periods (t1+n), and Converting subgroup values to matrix pixel values;
      generating an N×N matrix of (t1+n) matrix pixel values, and Generating a (t1+n) sensor signal pattern(s) from said (t1+n) matrix pixel values;
      comparing (t1+n) sensor signal pattern(s) against the (t1) signature sensor signal pattern; and
      wirelessly transmitting to the health data server the comparison of (t1+n) sensor signal pattern(s) against the (t1) signature sensor signal pattern.

12. The computer implemented method of claim 11, wherein the computer program instructions readable by the main on-body component microprocessor stored to memory perform the following additional steps in order:
   receiving at a health data server a comparison of (t1+n) sensor signal matrix pattern(s) against the (t1) signature sensor signal matrix pattern from a wireless multi-sensor continuous vital sign monitoring device,
   performing a best fit matching of the comparison of (t1+n) to (t1) sensor signal matrix patterns against a stored diagnostic array of sensor signal matrix patterns comprising diseases or disorders selected from pulmonary, cardiac, neurological, cardiovascular, orthopedic, pain, immune, and infection, and
   outputting to a patient communication device or healthcare provider access computer the best fit matching results, and provide intervention instructions related to the diseases or disorders selected from the group consisting of pulmonary, cardiac, neurological, cardiovascular, orthopedic, pain, immune, and infection from the stored diagnostic array of sensor signal matrix patterns.

13. The computer implemented method of claim 11, wherein the computer program instructions readable by the main on-body component microprocessor stored to memory perform the following additional steps in order:
   receiving at a health data server a comparison of (t1+n) sensor signal matrix pattern(s) against the (t1) signature sensor signal matrix pattern from a wireless multi-sensor continuous vital sign monitoring device, wherein the (t1+n) sensor signal matrix patterns and the (t1) signature sensor signal matrix pattern comprise a dynamic pixel-by-pixel clickable N×N matrix including the raw mean and standard deviation values from subgroups at period (t1) that form the (t1) matrix pixel value, and values from subgroups at periods (t1+n) that form the (t1+n) matrix pixel value, Identifying in a clickable display and clicking on one or more of the pixel(s) from the (t1+n) matrix pixel value of the (t1+n)

sensor signal matrix pattern having a large period-by-period change to obtain the raw mean and standard deviation values from sensor data subgroups to identify the specific sensors and times providing the large period-by-period change values, and outputting to a patient communication device or healthcare provider access computer change-specific patient intervention instructions related to the specific sensors and times of the large period-by-period changes.

14. The computer implemented method of claim 11, wherein the peripheral on-body-component is attached to a patient at a location selected from the group consisting of: hip, knee, neck, arm, wrist, forehead, occipital region, sternum, and shoulder.

15. The computer implemented method of claim 11, comprising two or more peripheral on-body-components, wherein the two or more peripheral on-body-components are attached to a patient at different locations selected from the group consisting of: hip, knee, neck, arm, wrist, forehead, occipital region, sternum, and shoulder.

* * * * *

UNITED STATES PATENT AND TRADEMARK OFFICE
CERTIFICATE OF CORRECTION

| | | |
|---|---|---|
| PATENT NO. | : 12,097,007 B2 | Page 1 of 1 |
| APPLICATION NO. | : 17/635696 | |
| DATED | : September 24, 2024 | |
| INVENTOR(S) | : Moon, Lee and Youm | |

It is certified that error appears in the above-identified patent and that said Letters Patent is hereby corrected as shown below:

In the Specification

Insert at Column 1, Line 4 before CROSS-REFERENCE TO RELATED APPLICATIONS, the following:
--FEDERALLY SPONSORED RESEARCH AND DEVELOPMENT
This invention was made with government support under Grant Number U54MD012397 awarded by the National Institutes of Health. The government has certain rights in the invention.--

Signed and Sealed this
Thirteenth Day of May, 2025

Coke Morgan Stewart
*Acting Director of the United States Patent and Trademark Office*